(12) United States Patent
Keenan et al.

(10) Patent No.: US 8,425,444 B2
(45) Date of Patent: Apr. 23, 2013

(54) ANTI-CLOTTING APPARATUS AND METHODS FOR FLUID HANDLING SYSTEM

(75) Inventors: Richard Keenan, Livermore, CA (US); Jeff Chiou, Union City, CA (US)

(73) Assignee: Optiscan Biomedical Corporation, Hayward, CA (US)

( * ) Notice: Subject to any disclaimer, the term of this patent is extended or adjusted under 35 U.S.C. 154(b) by 364 days.

(21) Appl. No.: 11/734,242

(22) Filed: Apr. 11, 2007

(65) Prior Publication Data

US 2007/0239096 A1 Oct. 11, 2007

Related U.S. Application Data

(60) Provisional application No. 60/791,621, filed on Apr. 11, 2006.

(51) Int. Cl.
*A61M 37/00* (2006.01)
(52) U.S. Cl.
USPC .......................................... 604/4.01; 500/573
(58) Field of Classification Search .................. 604/4.01; 600/573
See application file for complete search history.

(56) References Cited

U.S. PATENT DOCUMENTS

| | | |
|---|---|---|
| 2,797,149 A | 6/1957 | Skeggs |
| 3,251,229 A | 5/1966 | Isreeli et al. |
| 3,252,327 A | 5/1966 | Ferrrari |
| 3,266,322 A | 8/1966 | Negersmith et al. |
| 3,282,651 A | 11/1966 | Ferrari et al. |
| 3,352,303 A | 11/1967 | Delaney |
| 3,562,234 A | 2/1971 | Resz et al. |
| 3,565,062 A | 2/1971 | Kuris |
| 3,634,039 A | 1/1972 | Brondy |
| 3,910,256 A | 10/1975 | Clark et al. |
| 3,972,614 A | 8/1976 | Johansen et al. |
| 4,127,111 A | 11/1978 | Drolet |
| 4,151,845 A | 5/1979 | Clemens |
| 4,240,438 A | 12/1980 | Updike et al. |
| 4,245,634 A | 1/1981 | Albisser et al. |

(Continued)

FOREIGN PATENT DOCUMENTS

| | | |
|---|---|---|
| EP | 0549341 | 12/1992 |
| JP | 01-170031 | 6/2001 |

(Continued)

OTHER PUBLICATIONS

John A. Widness, et al; Pediatrics; Jun. 21, 2005; Downloaded from www.pediatrics.org on Jun. 21, 2005; "Clinical Performance of an In-Line Point-of-Care Monitor in Neonates."

(Continued)

*Primary Examiner* — Max Hindenburg
*Assistant Examiner* — Renee Danega
(74) *Attorney, Agent, or Firm* — Knobbe Martens Olson & Bear LLP

(57) ABSTRACT

Methods and apparatus are provided for determining the concentration of an analyte in a sample, such as an analyte in a sample of bodily fluid. In some embodiments, a method for maintaining clear passageways in an extracorporeal blood flow system includes intermittently providing one or more anti-clotting agents to a passageway of the extracorporeal blood flow system. In some embodiments, an extracorporeal blood flow system includes a passageway and a device operatively connected to provide one or more anti-clotting agents to a least a portion of said passageway.

39 Claims, 19 Drawing Sheets

U.S. PATENT DOCUMENTS

| | | | |
|---|---|---|---|
| 4,526,568 A | 7/1985 | Clemens et al. | |
| 4,526,569 A | 7/1985 | Bernardi | |
| 4,535,786 A | 8/1985 | Kater | |
| 4,568,545 A | 2/1986 | Mihara et al. | |
| 4,573,968 A | 3/1986 | Parker | |
| 4,613,322 A | 9/1986 | Edelson | |
| 4,657,027 A | 4/1987 | Paulsen | |
| 4,657,529 A | 4/1987 | Prince et al. | |
| 4,784,157 A | 11/1988 | Halls et al. | |
| 4,796,644 A | 1/1989 | Polaschegg | |
| 4,870,953 A | 10/1989 | DonMicheall et al. | |
| 4,919,596 A | 4/1990 | Slate et al. | |
| 4,934,369 A | 6/1990 | Maxwell | |
| 4,974,592 A | 12/1990 | Branco et al. | |
| 4,976,270 A | 12/1990 | Parl et al. | |
| 5,109,850 A | 5/1992 | Blanco et al. | |
| 5,134,079 A | 7/1992 | Cusack et al. | |
| 5,149,501 A | 9/1992 | Babson et al. | |
| 5,165,406 A | 11/1992 | Wong | |
| 5,269,291 A | 12/1993 | Carter | |
| 5,295,484 A | 3/1994 | Marcus et al. | |
| 5,300,779 A | 4/1994 | Hillman et al. | |
| 5,307,816 A | 5/1994 | Hashimoto et al. | |
| 5,335,658 A | 8/1994 | Bedingham | |
| 5,377,674 A | 1/1995 | Kuestner | |
| 5,380,665 A | 1/1995 | Cusack et al. | |
| 5,399,158 A | 3/1995 | Lauer et al. | |
| 5,421,328 A | 6/1995 | Bedingham | |
| 5,431,663 A | 7/1995 | Carter | |
| 5,505,828 A | 4/1996 | Wong et al. | |
| 5,524,620 A | 6/1996 | Rosenschein | |
| 5,620,409 A | 4/1997 | Venuto et al. | |
| 5,695,460 A | 12/1997 | Siegel et al. | |
| 5,697,366 A | 12/1997 | Kimball et al. | |
| 5,697,899 A * | 12/1997 | Hillman et al. | 604/28 |
| 5,722,397 A | 3/1998 | Eppstein | |
| 5,758,643 A | 6/1998 | Wong et al. | |
| 5,817,007 A | 10/1998 | Fodgaard et al. | |
| 5,827,746 A | 10/1998 | Duic | |
| 5,902,253 A | 5/1999 | Pfeiffer et al. | |
| 5,944,660 A | 8/1999 | Kimball et al. | |
| 5,947,911 A | 9/1999 | Wong et al. | |
| 6,007,499 A | 12/1999 | Martin et al. | |
| 6,017,318 A * | 1/2000 | Gauthier et al. | 600/578 |
| 6,025,597 A | 2/2000 | Sterling et al. | |
| 6,040,578 A | 3/2000 | Malin et al. | |
| 6,086,573 A | 7/2000 | Siegel et al. | |
| 6,101,406 A | 8/2000 | Hacker et al. | |
| 6,107,280 A | 8/2000 | White et al. | |
| 6,113,570 A | 9/2000 | Siegel et al. | |
| 6,117,290 A | 9/2000 | Say et al. | |
| 6,200,287 B1 | 3/2001 | Keller et al. | |
| 6,261,519 B1 | 7/2001 | Harding et al. | |
| 6,262,798 B1 | 7/2001 | Shepherd et al. | |
| 6,358,534 B1 | 3/2002 | Schwarz et al. | |
| 6,433,464 B2 | 8/2002 | Jones | |
| 6,461,586 B1 | 10/2002 | Unger | |
| 6,478,765 B2 | 11/2002 | Siegel et al. | |
| 6,491,656 B1 | 12/2002 | Morris | |
| 6,521,182 B1 | 2/2003 | Shartle et al. | |
| 6,652,136 B2 | 11/2003 | Marziali | |
| 6,685,657 B2 | 2/2004 | Jones | |
| 6,716,412 B2 | 4/2004 | Unger | |
| 6,733,450 B1 | 5/2004 | Alexandrov et al. | |
| RE38,869 E | 11/2005 | Polaschegg et al. | |
| 7,115,205 B2 | 10/2006 | Robinson et al. | |
| 7,126,676 B2 | 10/2006 | Greco | |
| 7,364,562 B2 | 4/2008 | Braig et al. | |
| 2002/0045525 A1 | 4/2002 | Marziali | |
| 2002/0076354 A1* | 6/2002 | Cohen | 422/72 |
| 2002/0098528 A1 | 7/2002 | Gordon et al. | |
| 2002/0198528 A1* | 12/2002 | Engh et al. | 606/79 |
| 2003/0086074 A1 | 5/2003 | Braig et al. | |
| 2003/0086075 A1 | 5/2003 | Braig et al. | |
| 2003/0090649 A1 | 5/2003 | Sterling et al. | |
| 2003/0178569 A1 | 9/2003 | Sterling et al. | |
| 2004/0019431 A1 | 1/2004 | Sterling et al. | |
| 2004/0082899 A1* | 4/2004 | Mathias et al. | 604/6.16 |
| 2004/0127841 A1* | 7/2004 | Briggs | 604/6.01 |
| 2004/0147034 A1 | 7/2004 | Gore et al. | |
| 2004/0241736 A1 | 12/2004 | Hendee et al. | |
| 2004/0249308 A1 | 12/2004 | Forssell | |
| 2005/0036146 A1 | 2/2005 | Braig et al. | |
| 2005/0036147 A1 | 2/2005 | Sterling et al. | |
| 2005/0037482 A1 | 2/2005 | Braig et al. | |
| 2005/0038357 A1 | 2/2005 | Hartstein et al. | |
| 2005/0203360 A1 | 9/2005 | Brauker et al. | |
| 2005/0238538 A1 | 10/2005 | Braig et al. | |
| 2005/0284815 A1* | 12/2005 | Sparks et al. | 210/645 |
| 2006/0009727 A1 | 1/2006 | O'Mahony et al. | |
| 2006/0029923 A1* | 2/2006 | Togawa et al. | 435/2 |
| 2006/0079809 A1 | 4/2006 | Goldberger et al. | |
| 2006/0166276 A1* | 7/2006 | Doyle et al. | 435/7.1 |
| 2006/0188407 A1 | 8/2006 | Gable et al. | |
| 2006/0189858 A1 | 8/2006 | Sterling et al. | |
| 2006/0189925 A1 | 8/2006 | Gable | |
| 2006/0189926 A1 | 8/2006 | Hall | |
| 2006/0194325 A1 | 8/2006 | Gable et al. | |
| 2006/0195045 A1 | 8/2006 | Gable et al. | |
| 2006/0195046 A1 | 8/2006 | Sterling et al. | |
| 2006/0195058 A1 | 8/2006 | Gable et al. | |
| 2006/0197015 A1 | 9/2006 | Sterling et al. | |
| 2006/0200070 A1 | 9/2006 | Callicoat et al. | |
| 2006/0200071 A1 | 9/2006 | Sterling et al. | |
| 2006/0229531 A1 | 10/2006 | Goldberger et al. | |
| 2006/0235348 A1 | 10/2006 | Callicoat et al. | |
| 2007/0060872 A1 | 3/2007 | Hall et al. | |
| 2007/0081626 A1 | 4/2007 | Rule et al. | |
| 2007/0082342 A1 | 4/2007 | Braig et al. | |
| 2007/0083090 A1 | 4/2007 | Sterling et al. | |
| 2007/0083091 A1 | 4/2007 | Sterling et al. | |
| 2007/0083143 A1 | 4/2007 | Braig et al. | |
| 2007/0083160 A1 | 4/2007 | Hall et al. | |
| 2007/0103678 A1 | 5/2007 | Sterling et al. | |
| 2007/0104616 A1 | 5/2007 | Keenan et al. | |
| 2007/0142720 A1 | 6/2007 | Ridder et al. | |
| 2007/0179435 A1 | 8/2007 | Braig et al. | |
| 2007/0179436 A1 | 8/2007 | Braig et al. | |
| 2007/0225675 A1 | 9/2007 | Robinson et al. | |
| 2007/0258083 A1 | 11/2007 | Heppell et al. | |
| 2007/0278384 A1 | 12/2007 | Heppell | |
| 2009/0143711 A1 | 6/2009 | Braig et al. | |
| 2010/0273738 A1 | 10/2010 | Valcke et al. | |

FOREIGN PATENT DOCUMENTS

| | | | |
|---|---|---|---|
| WO | WO 02/38201 | * | 5/2002 |
| WO | WO 02/43866 | | 6/2002 |
| WO | WO 03/016882 | | 2/2003 |
| WO | WO 03/039362 | | 5/2003 |
| WO | WO 2004/092715 A1 | | 10/2004 |
| WO | WO 2005/110601 A1 | | 11/2005 |

OTHER PUBLICATIONS

Javier Daniel Finkielman, et al; "Agreement Between Bedside Blood and Plasma Glucose Measurement in the ICU Setting"; www.chestjournal.org; CHEST/127/5 May 2005.

Fogt, et al, "Development and Evaluation of a Glucose Analyzer for a Glucose-Controlled Insulin Infusion System (Biostator)"; Clinical Chemistry, vol. 24, No. 8, 1978.

Berger, et al; "An Enhanced Algorithm for Linear Multivariate"; Analytical Chemistry, vol. 70, No. 3, Feb. 1, 1998.

Ray, et al.; Critical Care Medicine, vol. 29, No. 11 (Nov. 2001) Reference Collection WI CR216K Nov. 20, 2001 07:00:41; "Pilot study of the accuracy of bedside glucometry in the intensive care unit."

Glenn F. Billman, et al.; "Clinical Performance of an In-Line, ex Vivo Point-of-Care Monitor: A Multicenter Study"; Clinical Chemistry 48:11 2030-2043 (2002).

Raelene E. Maser PhD., et al.; Critical Care Medicine, vol. 22/No. 4, Apr. 1994; "Use of arterial blood with bedside glucose reflectance meters in an intensive care unit: Are they accurate?"

Glucon Critical Care Blood Glucose Monitor Product Description; retrieved from http://www.glucon.com.

International Search Report dated Feb. 1, 2008, Application No. PCT/US2007/008998.

Co-pending application assigned to the assignee of the current application: U.S. Appl. No. 11/316,676.
Co-pending application assigned to the assignee of the current application: U.S. Appl. No. 11/316,205.
Co-pending application assigned to the assignee of the current application: U.S. Appl. No. 11/504,444.
Co-pending application assigned to the assignee of the current application: U.S. Appl. No. 11/504,327.
Co-pending application assigned to the assignee of the current application: U.S. Appl. No. 11/504,326.
Co-pending application assigned to the assignee of the current application: U.S. Appl. No. 11/839,487.
Co-pending application assigned to the assignee of the current application: U.S. Appl. No. 11/839,447.
Co-pending application assigned to the assignee of the current application: U.S. Appl. No. 11/850,972.

International Search Report dated Nov. 22, 2006, Application No. PCT/US2006/004930.
Franchini, Massimo, "Heparin-induced thrombocytopenia: an update", Thrombosis Journal, Oct. 4, 2005, vol. 3, Issue 14.
Office Action dated Sep. 3, 2010, U.S. Appl. No. 12/111,109, filed Feb. 28, 2008.
Response to Office Action filed Dec. 3, 2010, U.S. Appl. No. 12/111,109, filed Feb. 28, 2008.
Office Action dated Feb. 17, 2011, U.S. Appl. No. 12/111,109, filed Feb. 28, 2008.
Response to Office Action filed May 9, 2011, U.S. Appl. No. 12/111,109, filed Feb. 28, 2008.

* cited by examiner

ANTI-CLOTTING APPARATUS AND METHODS FOR FLUID HANDLING SYSTEM

PRIORITY INFORMATION

This application claims priority to U.S. Provisional Patent Application No. 60/791,621, filed Apr. 11, 2006, the entirety of which is hereby incorporated by reference and made part of this specification.

BACKGROUND

1. Field

Certain embodiments disclosed herein relate to methods and apparatus for determining the concentration of an analyte in a sample, such as an analyte in a sample of bodily fluid, as well as methods and apparatus which can be used to support the making of such determinations.

2. Description of the Related Art

It is a common practice to measure the levels of certain analytes, such as glucose, in a bodily fluid, such as blood. Often this is done in a hospital or clinical setting when there is a risk that the levels of certain analytes may move outside a desired range, which in turn can jeopardize the health of a patient. Certain currently known systems for analyte monitoring in a hospital or clinical setting suffer from various drawbacks.

SUMMARY

Embodiments described herein have several features, no single one of which is solely responsible for their desirable attributes. Without limiting the scope of the invention as expressed by the claims, some of the advantageous features will now be discussed briefly.

Some embodiments comprise a method for maintaining clear passageways in an extracorporeal blood flow system. The method can comprise intermittently providing one or more anti-clotting agents to a passageway of the extracorporeal blood flow system. In some embodiments, intermittently providing one or more anti-clotting agents comprises intermittently providing ultrasonic energy to the passageway. In some embodiments, intermittently providing one or more anti-clotting agents to a passageway of the extracorporeal blood flow system comprises delivery of a cleaning solution that is thermally stable at room temperatures. In some embodiments, intermittently providing one or more anti-clotting agents to a passageway of the extracorporeal blood flow system comprises delivery of a mixture having approximately 1% TERGAZYME in saline. In some embodiments, intermittently providing one or more anti-clotting agents to a passageway of the extracorporeal blood flow system comprises delivery of a mixture comprising sodium heparin. In some embodiments, intermittently providing one or more anti-clotting agents to a passageway of the extracorporeal blood flow system comprises delivery of a mixture comprising $K_2EDTA$. In some embodiments, intermittently providing one or more anti-clotting agents to a passageway of the extracorporeal blood flow system comprises delivery of a mixture comprising $K_3EDTA$. In some embodiments, intermittently providing one or more anti-clotting agents to a passageway of the extracorporeal blood flow system comprises delivery of a mixture comprising Potassium Oxalate/sodium fluoride. In some embodiments, intermittently providing one or more anti-clotting agents to a passageway of the extracorporeal blood flow system comprises delivery of a mixture comprising Sodium Citrate/Citric acid.

Some embodiments comprise an extracorporeal blood flow system comprising a passageway and a device operatively connected to the passageway to provide one or more anti-clotting agents to a least a portion of said passageway. In some embodiments, the system further comprises: a bubble injector configured to separate drawn blood into an analyze and return portions; a waste bladder configured to receive the analyze portion after it is analyzed; and a pump configured to return the return portion to a patient.

Some embodiments comprise an apparatus for preventing blood coagulation in a blood flow system. The apparatus can comprise: a blood flow passageway; and an ultrasonic vibration device configured to transmit ultrasonic energy into the flow passageway. In some embodiments, the ultrasonic vibration device comprises an ultrasonic generator and an ultrasonic horn. In some embodiments, the ultrasonic vibration device is movable and can be placed in contact with a blood-containing portion of the blood flow system. In some embodiments, the ultrasonic vibration device is configured to transmit energy at a frequency in the range of approximately 15 to 60 kHz.

Some embodiments comprise a method of correcting an analyte measurement for dilution. The method can comprise: determining a ratio of volume of anticoagulant solution to total volume; using the equation $C0=C0'(1+\delta V/V0)$ to correct for dilution; and storing the corrected measurement in a memory. In some embodiments, the method can further comprise: providing an accurately-measured volume of anticoagulant solution; and measuring the amount of anticoagulation analyte in the sampling system.

Certain objects and advantages of the invention(s) are described herein. Of course, it is to be understood that not necessarily all such objects or advantages may be achieved in accordance with any particular embodiment. Thus, for example, those skilled in the art will recognize that the invention(s) may be embodied or carried out in a manner that achieves or optimizes one advantage or group of advantages as taught herein without necessarily achieving other objects or advantages as may be taught or suggested herein.

Certain embodiments are summarized above. The summarized embodiments, and other embodiments, will become readily apparent to those skilled in the art from the following detailed description of the preferred embodiments having reference to the attached figures, the invention(s) not being limited to any particular embodiment(s) disclosed.

BRIEF DESCRIPTION OF THE DRAWINGS

The following drawings and the associated descriptions are provided to illustrate embodiments of the present disclosure and do not limit the scope of the claims.

Reference symbols are used in the Figures to indicate certain components, aspects or features shown therein, with reference symbols common to more than one Figure indicating like components, aspects or features shown therein.

DETAILED DESCRIPTION OF THE PREFERRED EMBODIMENTS

Although certain preferred embodiments and examples are disclosed below, the inventive subject matter extends beyond the specifically disclosed embodiments to other alternative embodiments and/or uses of the invention, and to modifications and equivalents thereof. Thus, the scope of the inventions herein disclosed is not limited by any of the particular embodiments described below. For example, in any method or process disclosed herein, the acts or operations of the method or process may be performed in any suitable sequence and are not necessarily limited to any particular disclosed sequence. For purposes of contrasting various embodiments with the prior art, certain aspects and advantages of these embodiments are described. Of course, it is to be understood that not necessarily all such aspects or advantages are achieved by any particular embodiment. Thus, for example, it should be recognized that the various embodiments may be carried out in a manner that achieves or optimizes one advantage or group of advantages as taught herein without necessarily achieving other aspects or advantages as may be taught or suggested herein. The systems and methods discussed herein can be used anywhere, including, for example, in laboratories, hospitals, healthcare facilities, intensive care units (ICUs), or residences. Moreover, the systems and methods discussed herein can be used for invasive techniques, as well as non-invasive techniques or techniques that do not involve a body or a patient.

Figure 1:
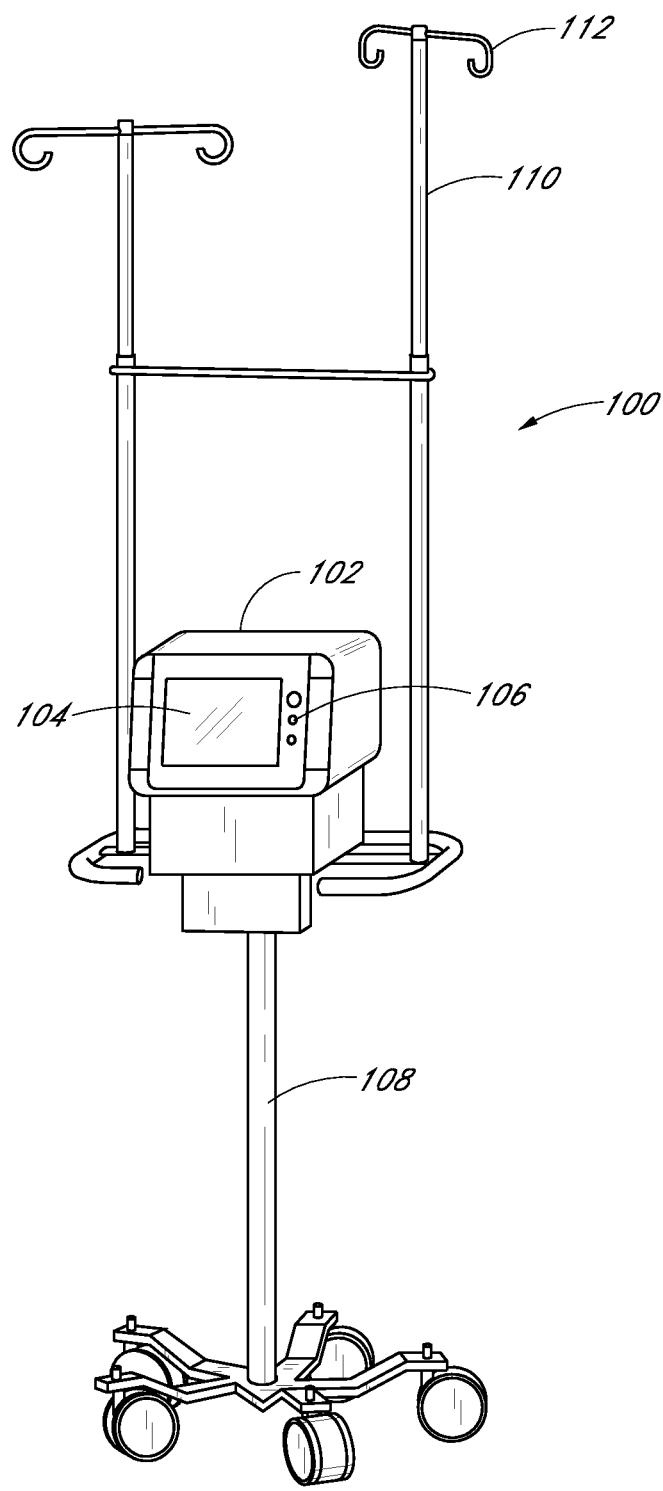
FIG. 1 shows an embodiment of an apparatus for withdrawing and analyzing fluid samples.

FIG. 1 shows an embodiment of an apparatus 100 for withdrawing and analyzing fluid samples. The apparatus 100 includes a monitoring device 102. In some embodiments, the monitoring device 102 can be an "OptiScanner®," available from OptiScan Biomedical Corporation of Hayward, Calif. In some embodiments, the device 100 can measure one or more physiological parameters, such as the concentration of one or more substance(s) in a sample fluid. The sample fluid can be, for example, whole blood from a patient 302 (see, e.g., FIG. 3). In some embodiments, the device 100 can also deliver an infusion fluid to the patient 302.

In the illustrated embodiment, the monitoring device 102 includes a display 104 such as, for example, a touch-sensitive liquid crystal display. The display 104 can provide an interface that includes alerts, indicators, charts, and/or soft buttons. The device 102 also can include one or more inputs and/or outputs 106 that provide connectivity.

In the embodiment shown in FIG. 1, the device 102 is mounted on a stand 108. The stand 108 can be easily moved and includes one or more poles 110 and/or hooks 112. The poles 110 and hooks 112 can be configured to accommodate other medical implements, including, for example, infusion pumps, saline bags, arterial pressure sensors, other monitors and medical devices, and so forth.

Figure 2:
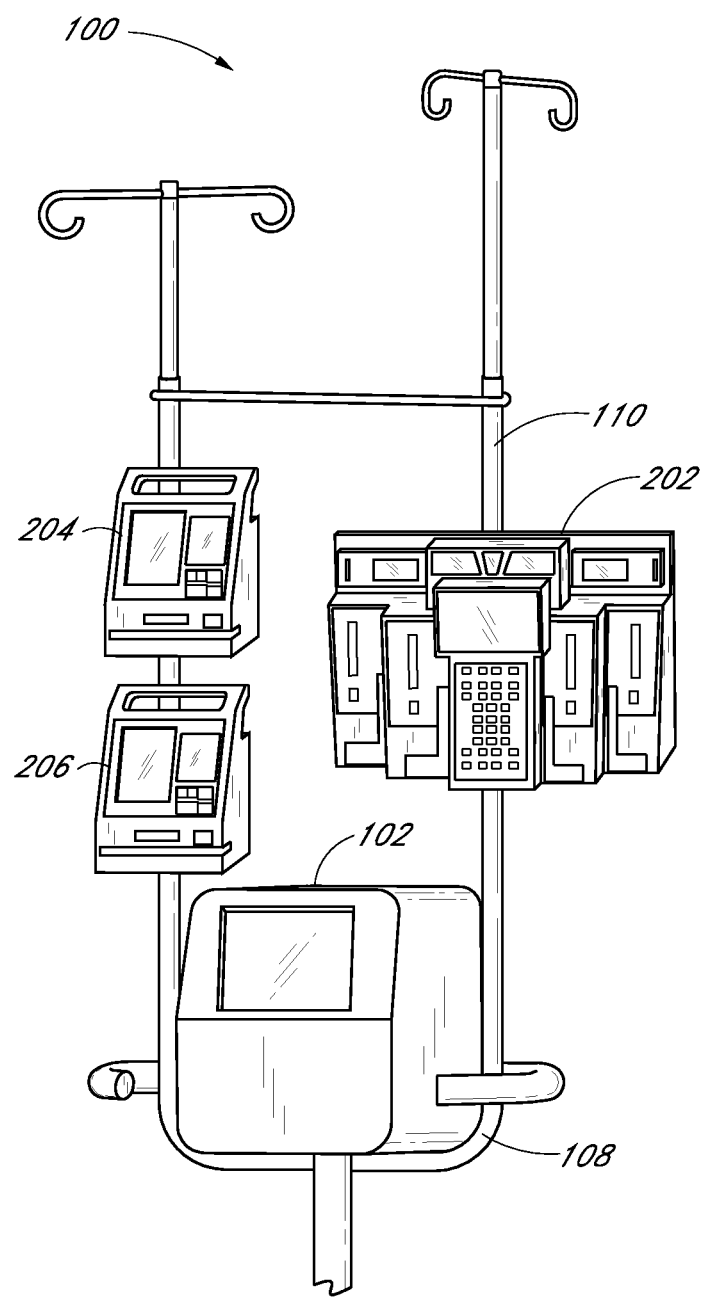
FIG. 2 illustrates how various other devices can be supported on or near an embodiment of apparatus illustrated in FIG. 1.

FIG. 2 illustrates how various other devices can be supported on or near the apparatus 100 illustrated in FIG. 1. For example, the poles 110 of the stand 108 can be configured (e.g., of sufficient size and strength) to accommodate multiple devices 202, 204, 206. In some embodiments, one or more COLLEAGUE® volumetric infusion pumps available from Baxter International Inc. of Deerfield, Ill. can be accommodated. In some embodiments, one or more Alaris® PC units available from Cardinal Health, Inc. of Dublin, Ohio can be accommodated. Furthermore, various other medical devices (including the two examples mentioned here), can be integrated with the disclosed monitoring device 102 such that multiple devices function in concert for the benefit of one or multiple patients without the devices interfering with each other.

Figure 3:
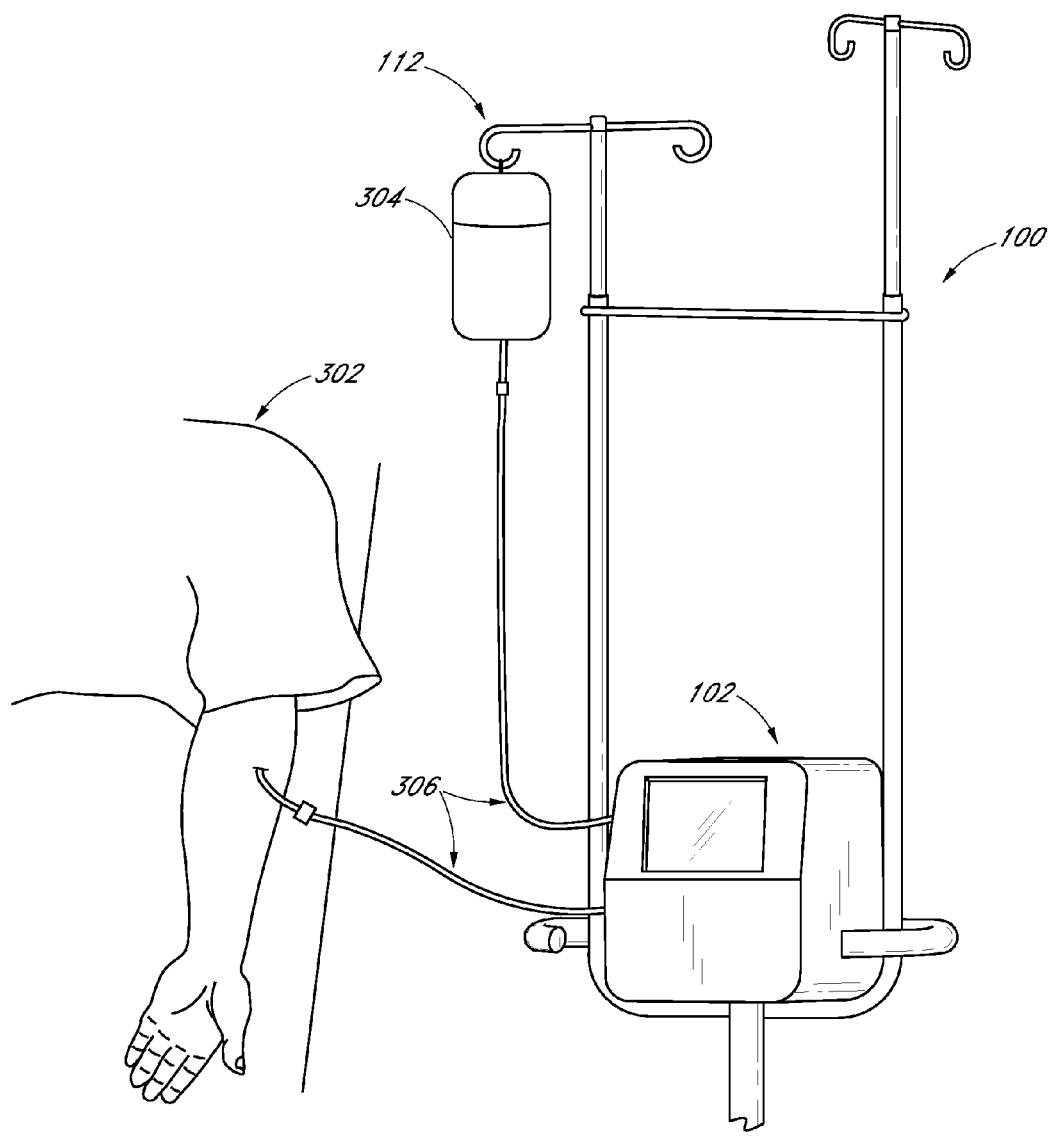
FIG. 3 illustrates an embodiment of the apparatus in FIG. 1 connected to a patient.

FIG. 3 illustrates the apparatus 100 of FIG. 1 as it can be connected to a patient 302. The monitoring device 102 can be used to determine the concentration of one or more substances in a sample fluid. The sample fluid can come from a fluid container in a laboratory setting, or it can come from a patient 302, as illustrated here. In some preferred embodiments, the sample fluid is whole blood.

In some embodiments, the monitoring device 102 can also deliver an infusion fluid to the patient 302. An infusion fluid container 304 (e.g., a saline bag), which can contain infusion fluid (e.g., saline and/or medication), can be supported by the hook 112. The monitoring device 102 can be in fluid communication with both the container 304 and the sample fluid source (e.g., the patient 302), through tubes 306. The infusion fluid can comprise any combination of fluids and/or chemicals. Some advantageous examples include (but are not limited to): water, saline, dextrose, lactated Ringer's solution, drugs, and insulin.

The illustrated monitoring device 102 allows the infusion fluid to pass to the patient 302 and/or uses the infusion fluid itself (e.g., as a flushing fluid or a standard with known optical properties, as discussed further below). In some embodiments, the monitoring device 102 may not employ infusion fluid. The monitoring device 102 may thus draw samples without delivering any additional fluid to the patient 302. The monitoring device 102 can include, but is not limited to, fluid handling and analysis apparatuses, connectors, passageways, catheters, tubing, fluid control elements, valves, pumps, fluid sensors, pressure sensors, temperature sensors, hematocrit sensors, hemoglobin sensors, calorimetric sensors, gas (e.g., "bubble") sensors, fluid conditioning elements, gas injectors, gas filters, blood plasma separators, and/or communication devices (e.g., wireless devices) to permit the transfer of information within the monitoring device 102 or between the monitoring device 102 and a network.

In some embodiments, one or more components of the apparatus 100 can be located at another facility, room, or other suitable remote location. One or more components of the monitoring device 102 can communicate with one or more other components of the monitoring device 102 (or with other devices) by communication interface(s) such as, but not limited to, optical interfaces, electrical interfaces, and/or wireless interfaces. These interfaces can be part of a local network, internet, wireless network, or other suitable networks.

System Overview

Figure 4:
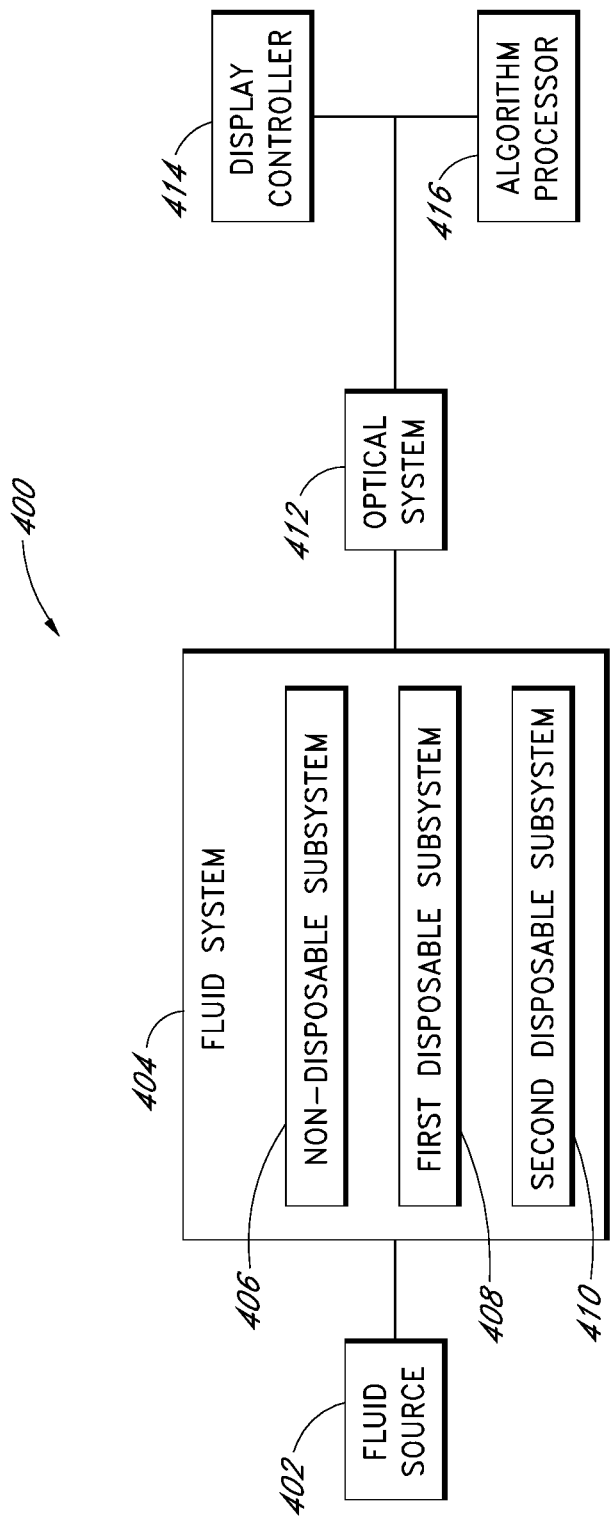
FIG. 4 is a block diagram of an embodiment of a system for withdrawing and analyzing fluid samples.

FIG. 4 is a block diagram of a system 400 for withdrawing and analyzing fluid samples. The monitoring device 102 can comprise such a system. The system 400 includes a fluid source 402 connected to a fluid system 404. The fluid system 404 prepares fluid samples that are analyzed by an optical system 412. The system 400 includes a display controller 414 and an algorithm processor 416 that assist in fluid sample analysis and presentation of data. In some embodiments, the sampling and analysis system 400 is a mobile point of care apparatus that monitors physiological parameters such as, for example, blood glucose concentration. Tubes and connectors within the system 400 can be coated with an antibacterial coating to reduce the risk of infection. Connectors between at least some components of the system 400 can include a self-sealing valve, such as a spring valve, in order to reduce the risk of contact between port openings and fluids, and to guard against fluid escaping from the system.

Fluid Source 402

The sampling and analysis system 400 includes a fluid source 402 that contains fluid to be sampled. The fluid system 404 of the sampling and analysis system 400 is connected to a fluid source 402 from which fluid samples can be drawn. The fluid source 402 can be, for example, a patient's blood vessel such as a vein or an artery, a container such as a decanter or a tube, or any other corporeal or extracorporeal fluid source. The fluid to be sampled can be, for example, blood, plasma, or another bodily fluid.

Fluid System 404

In some embodiments, the fluid system 404 withdraws a sample of fluid from the fluid source 402 for analysis, centrifuges at least a portion of the sample, and prepares at least a portion of the sample for analysis by an optical sensor such as a spectrophotometer. In some embodiments, at least a portion of the sample is returned to the fluid source 402. At least some of the sample, such as portions of the sample that are mixed with other materials or portions that are otherwise altered during the sampling and analysis process, can also be placed in a waste bladder. The waste bladder can be integrated within the fluid system 404 or supplied by a user of system 400. The fluid system 404 can also be connected to a saline source, a detergent source, and/or an anticoagulant source, each of which can be supplied by a user or integrated within fluid system 404.

Components of the fluid system 404 can be modularized into one or more non-disposable, disposable, and/or replaceable subsystems. In the embodiment shown in FIG. 4, components of the fluid system 404 are separated into a non-disposable subsystem 406, a first disposable subsystem 408, and a second disposable subsystem 410.

The non-disposable subsystem 406 can include components that do not generally require regular replacement during the useful lifetime of the system 400. In some embodiments, the non-disposable subsystem 406 of the fluid system 404 includes one or more reusable valves and sensors. For example, the non-disposable subsystem 406 can include one or more pinch valves (or non-disposable portions thereof), ultrasonic bubble sensors, non-contact pressure sensors, and optical blood dilution sensors. The non-disposable subsystem 406 can also include one or more pumps (or non-disposable portions thereof). In some embodiments, the components of the non-disposable subsystem 406 are not directly exposed to fluids and/or are not readily susceptible to contamination.

First and second disposable subsystems 408, 410 can include components that are regularly replaced under certain circumstances in order to facilitate the operation of the system 400. For example, the first disposable subsystem 408 can be replaced after a certain period of use, such as a few days, has elapsed. Replacement may be necessary, for example, when a bladder within the first disposable subsystem 408 is filled to capacity. Such replacement may mitigate fluid system performance degradation associated with and/or contamination wear on system components.

In some embodiments, the first disposable subsystem 408 includes components that may contact fluids such as patient blood, saline, flushing solutions, anticoagulants, and/or detergent solutions. For example, the first disposable subsystem 408 can include one or more tubes, fittings, cleaner pouches and/or waste bladders. The components of the first disposable subsystem 408 can be sterilized in order to decrease the risk of infection and can be configured to be easily replaceable.

In some embodiments, the second disposable subsystem 410 can be designed to be replaced under certain circumstances. For example, the second disposable subsystem 410 can be replaced when the patient being monitored by the system 400 is changed. The components of the second disposable subsystem 410 may not need replacement at the same intervals as the components of the first disposable subsystem 408. For example, the second disposable subsystem 410 can include a flow cell and/or at least some components of a centrifuge, components that may not become filled or quickly worn during operation of the system 400. Replacement of the second disposable subsystem 410 can decrease or eliminate the risk of transferring fluids from one patient to another during operation of the system 400, enhance the measurement performance of system 400, and/or reduce the risk of contamination or infection.

In some embodiments, the flow cell of the second disposable subsystem 410 receives the sample obtained from the fluid source 402 via the fluidics of the first disposable subsystem 408. The flow cell is a container that can hold fluid for the centrifuge and provide a window to the sample for analysis by a spectrometer. In some embodiments, the flow cell includes windows that are made of a material that is substantially transparent to electromagnetic radiation in the mid-infrared range of the spectrum. For example, the flow cell windows can be made of calcium fluoride.

An injector can provide a fluidic connection between the first disposable subsystem 408 and the flow cell. In some embodiments, the injector can be removed from the flow cell to allow for free spinning of the flow cell during centrifugation.

In some embodiments, the components of the sample are separated by centrifuging at a high speed for a period of time before measurements are performed by the optical system 412. For example, a blood sample can be centrifuged at 7200 RPM for 2 minutes in order to separate plasma from other blood components for analysis. Separation of a sample into the components can permit measurement of solute (e.g., glucose) concentration in plasma, for example, without interference from other blood components. This kind of post-separation measurement, (sometimes referred to as a "direct measurement") has advantages over a solute measurement taken from whole blood because the proportions of plasma to other components need not be known or estimated in order to infer plasma glucose concentration.

An anticoagulant, such as, for example, heparin can be added to the sample before centrifugation to prevent clotting. The fluid system 404 can be used with a variety of anticoagulants, including anticoagulants supplied by a hospital or other user of the monitoring system 400. A detergent solution formed by mixing detergent powder from a pouch connected to the fluid system 404 with saline can be used to periodically clean residual protein and other sample remnants from one or more components of the fluid system 404, such as the flow cell. Sample fluid to which anticoagulant has been added and used detergent solution can be transferred into the waste bladder.

Optical System 412

The system 400 shown in FIG. 4 includes an optical system 412 that can measure optical properties (e.g., transmission) of a fluid sample (or a portion thereof). In some embodiments, the optical system 412 measures transmission in the mid-infrared range of the spectrum. In some embodiments, the optical system 412 includes a spectrometer that measures the transmission of broadband infrared light through a portion of a flow cell filled with fluid. The spectrometer need not come in direct contact with the sample. As used herein, the term "flow cell" is a broad term that carries its ordinary meaning as an object that can provide a place for fluid. The fluid can enter the flow cell by flowing.

In some embodiments, the optical system 412 includes a filter wheel that contains one or more filters. In some embodiments, twenty-five filters are mounted on the filter wheel. The optical system 412 includes a light source that passes light through a filter and the flow cell to a detector. In some embodiments, a stepper motor moves the filter wheel in order to position a selected filter in the path of the light. An optical encoder can also be used to finely position one or more filters.

Display Controller 414

Figure 14A:
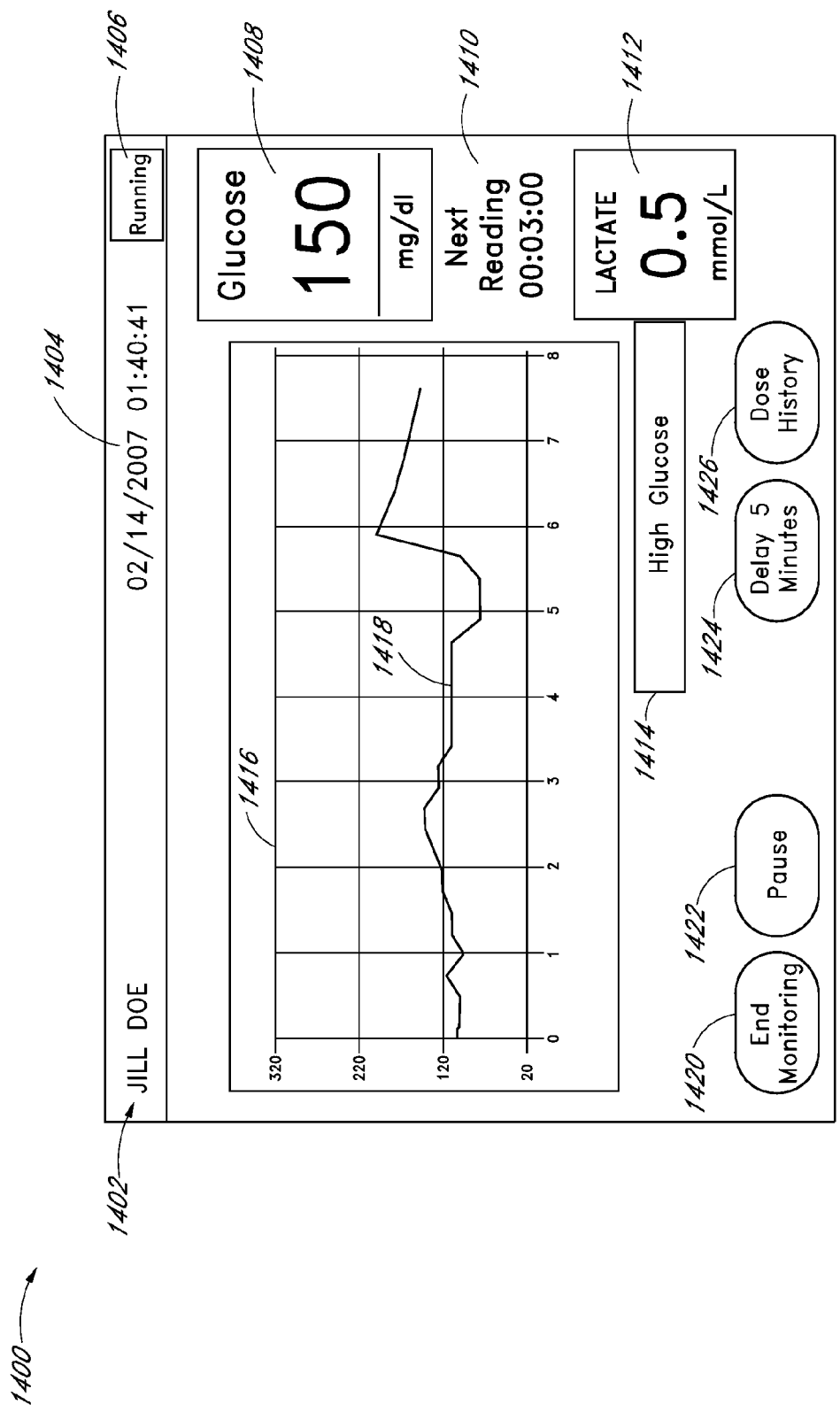
FIGS. 14A and 14B schematically illustrate the visual appearance of embodiments of a user interface for a system for withdrawing and analyzing fluid samples.
Figure 14B:
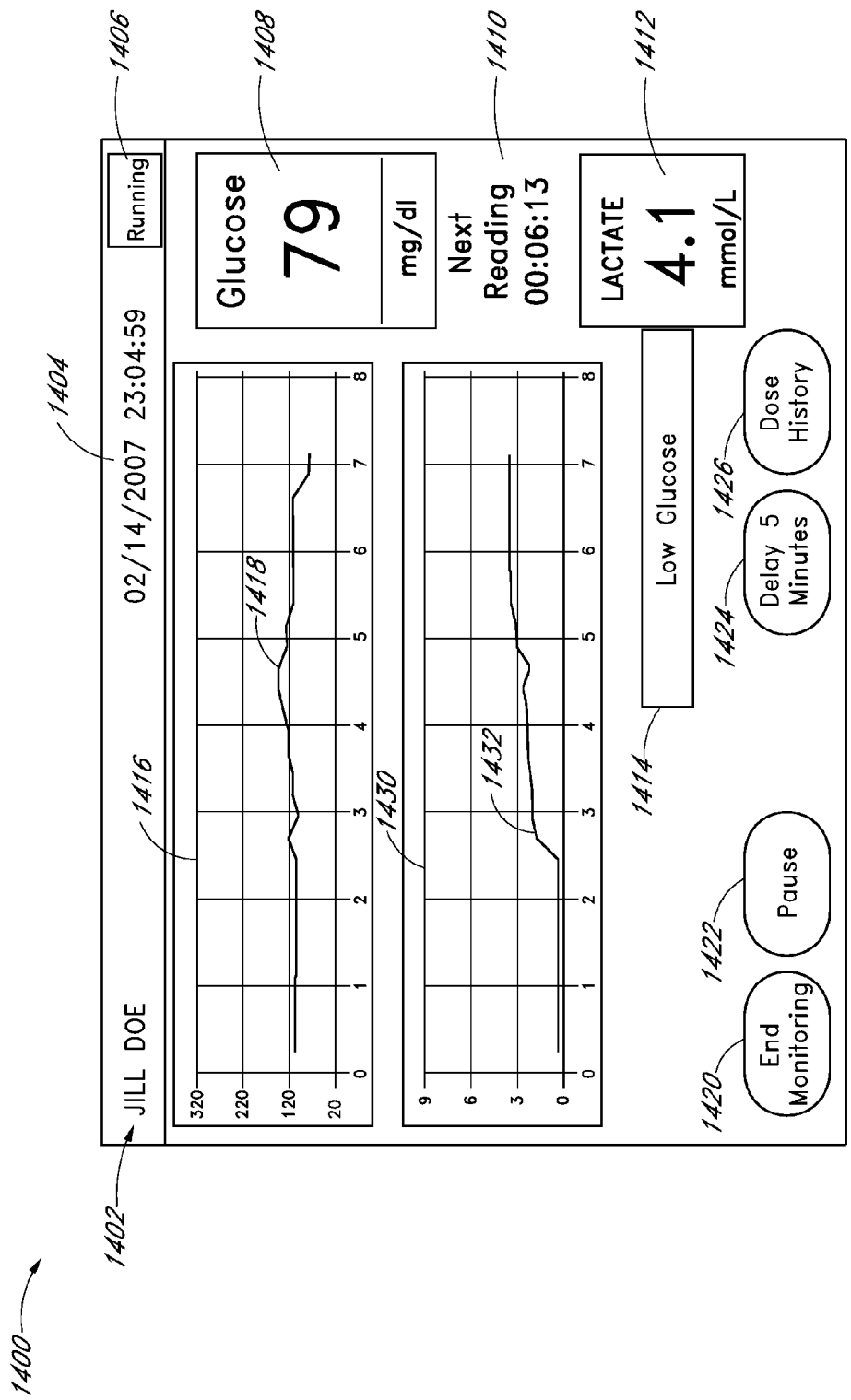

The system 400 shown in FIG. 4 includes a display controller 414 that provides for communication of information to a user of the system 400. The display controller 414 can include a display processor that controls or produces an interface to communicate information to the user. The display controller 414 can include a display screen. One or more parameters such as, for example, blood glucose concentration, system 400 operating parameters, and/or other operating parameters can be displayed on a monitor (not shown) associated with the system 400. An example of one way such information can be displayed is shown in FIGS. 14A and 14B. In some embodiments, the display controller 414 can communicate measured physiological parameters and/or operating parameters to a computer system over a communications connection.

Algorithm Processor 416

The system 400 shown in FIG. 4 includes an algorithm processor 416 that can receive optical density (OD) values (or other analog or digital optical data) from the optical system 412. In some embodiments, the algorithm processor 416 calculates one or more physiological parameters by adjusting the coefficients of a model, if necessary, and computing the physiological parameters using an equation having the adjusted coefficients. The algorithm processor 416, the display controller 414, and any embedded controllers within system 400 can be connected to one another with a communications bus.

Fluidics System

Figure 5:
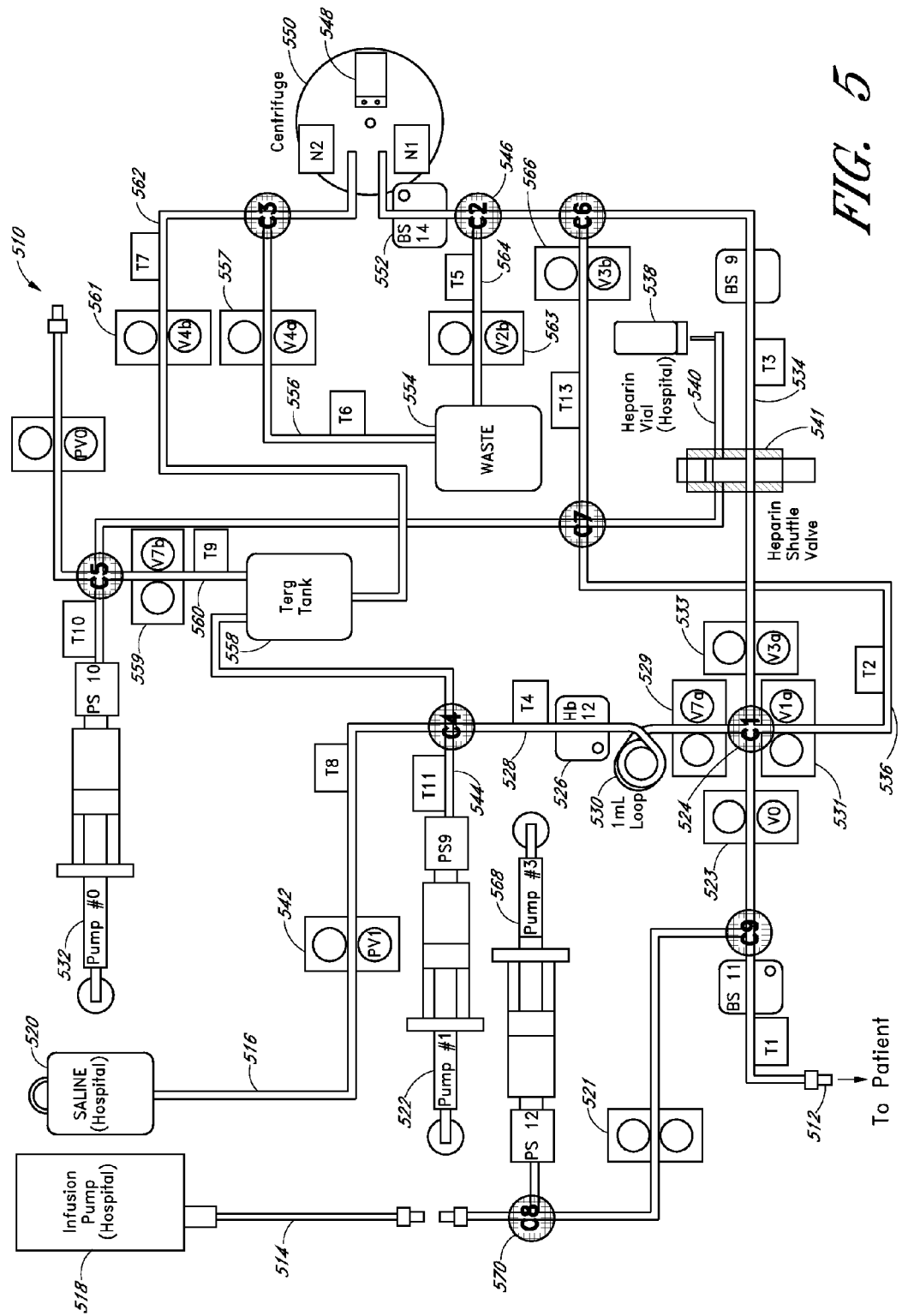
FIG. 5 schematically illustrates an embodiment of a fluid system within a system for withdrawing and analyzing fluid samples.

FIG. 5 schematically illustrates a fluid system 510. In addition to the reference numerals used below, the various portions of the illustrated fluid system 510 are labeled with letters to suggest their role as follows: T# indicates a section of tubing. C# indicates a connector that joins multiple tubing sections. V# indicates a valve. BS # indicates a bubble sensor or ultrasonic air detector. N# indicates a needle (e.g., a needle that injects sample into a flow cell). PS# indicates a pressure sensor (e.g., a reusable pressure sensor). Pump# indicates a fluid pump (e.g., a syringe pump with a disposable body and reusable drive). "Hb 12" indicates a sensor for hemoglobin (e.g., a dilution sensor that can detect hemoglobin optically).

At the start of a measurement cycle, most lines, including the patient tube 512 (T1), can be filled with saline that can be introduced into the system through the tubes 514 and 516, and which can come from an infusion pump 518 and/or a saline bag 520. The infusion pump 518 and the saline bag 520 can be provided separately from the system 510. For example, a hospital can use existing saline bags and infusion pumps to interface with the described system. The valve 521 can be open to allow saline to flow into the tube 512 (T1).

To draw a sample, a first pump 522 (pump #1) draws sample fluid to be analyzed (e.g. blood) from a fluid source (e.g., a laboratory sample container, a living patient, etc.) up into the patient tube 512 (T1), through the open valve F23 (V0), through the first connector 524 (C1), past the hemoglobin sensor 526 (Hb12), and into the looped tube 528 (T4). During this process, the valve 529 (V7a) is open to fluid flow, but the valves 531 (V1a) and 533 (V3a) can be closed and therefore block (or substantially block) fluid flow.

Initially the lines are filled with saline and the hemoglobin (Hb) level is zero. The tubes that are filled with saline are in fluid communication with the a sample source (not shown). The sample source can be the vessels of a living human or a pool of liquid in a laboratory sample container, for example. When the saline is drawn toward the first pump 522, fluid to be analyzed is also drawn into the system because of the suction forces in the closed fluid system. Thus, the first pump 522 draws a relatively continuous column of fluid that first comprises generally nondiluted saline, then a mixture of saline and sample fluid (e.g., blood), and then eventually nondiluted sample fluid. In the example illustrated here, the sample fluid is blood.

The hemoglobin sensor 526 (Hb12) detects the level of Hemoglobin in the sample fluid. As blood starts to arrive at the hemoglobin sensor 526 (Hb12), the hemoglobin level rises. When the hemoglobin level reaches a preset value (e.g., which can occur after a draw of approximately 2 mL depending on the size of the catheter used) there is a nondiluted sample present at the first connector 524 (C1). A nondiluted sample can be, for example, a blood sample that is not diluted with saline solution, but instead has the characteristics of the rest of the blood flowing through a patient's body. A loop of tubing 530 (e.g., a 1-mL loop) can be advantageously positioned as illustrated to help insure that undiluted fluid (e.g., undiluted blood) is present at the first connector 524 (C1) when the hemoglobin sensor 526 registers that the preset Hb threshold is crossed. The loop of tubing 530 provides additional length to the tube 528 (T4) to make it less likely that the portion of the fluid column in the tubing at the first connector 524 (C1) has advanced all the way past the mixture of saline and sample fluid, and the nondiluted blood portion of that fluid has reached the first connector 524 (C1).

When nondiluted blood is present at the first connector 524 (C1), a second pump 532 (pump #0) draws four "slugs" of blood into the tubing 534 (T3). As used herein, the term "slug" refers to a continuous column of fluid. Slugs can be separated from one another by injecting (or sucking in) small amounts of air to create bubbles at intervals in the tube. In the illustrated embodiment, blood slugs are alternated with air bubbles by maintaining the valve 523 (V0) closed, maintaining the valve 533 (V3a) open, and alternately closing and opening the valves 529 (V7a) and 531 (V1a) such that one is closed while the other one is open. This periodically pulls either one or the other of 1) blood from the tube 528 (T4) through the valve 529 (V7a) and 2) air from the tube 536 (T2) through the valve 531 (V1a). In some embodiments, four blood slugs are created. The first three blood slugs are approximately 15 µL and the fourth is approximately 35 µL.

As, or after, the slugs are formed, heparin can be inserted into each slug. A heparin vial 538 (e.g., an insertable vial provided independently by the user of the system 510) can be connected to a tube 540. A shuttle valve 541 can connect to both the tube 540 and the tube 534 (T3). The valve can open the tube 540 to a suction force (e.g., created by the pump 532), allowing heparin to be drawn from the vial 538 into the valve 541. Then, the shuttle valve 541 can slide the heparin over into fluid communication with the tube 534. The shuttle valve 541 can then return to its previous position. Thus, heparin can be shuttled from the tube 540 into the tube 534 (T3) such that each blood slug contains a precisely controlled amount of heparin.

Following the formation of four blood slugs, the majority of the sampled blood is returned to the patient. The first pump 522 (pump #1) pushes the blood out of the tube 528 (T4) and back to the patient by opening the valve 523 (V0), closing the valves 531 (V1a) and 533 (V3a), and keeping the valve 529 (V7a) open. The tube 528 (T4) is preferably flushed with approximately 2 mL of saline. This can be accomplished by closing the valve 529 (V7a), opening the valve 542 (PV1), drawing saline from the saline source 520 into the tube 544, closing the valve 542 (PV1), opening the valve 529 (V7a), and forcing the saline down the tube 528 (T4) with the pump 522.

In some embodiments, less than two minutes elapses between the time that blood is drawn from the patient and the time that the blood is returned to the patient after formation of the blood slugs.

Following return of the unused patient blood sample, the four slugs are pushed up the tube 534 (T3), through the second connector 546 (C2), and into the flow cell 548, which can be located on the centrifuge wheel 550. The bubble sensor 552 (BS14) can identify the fourth slug by identifying and counting how many air bubbles (or inter-slug spaces) pass by the sensor. The fourth slug can be identified, and the pump 522 can stop forcing the fluid column through the tube 534 so that the fourth slug remains within the flow cell 548. Thus, the first three blood slugs can serve to flush any residual saline out the flow cell 548. The three leading slugs can be deposited in the waste bladder 554 by passing through the tube F56 (T6) and through the valve 557 (V4a).

In some embodiments, the fourth blood slug is centrifuged for two minutes at 7200 RPM. This separates the whole blood into its components, isolates the plasma, and positions the plasma in the flow cell 548 for measurement. The centrifuge 550 is stopped with the flow cell 548 in a beam of radiation (not shown) for analysis. The radiation, a detector, and logic can be used to analyze the plasma spectroscopically (e.g., for glucose and/or lactate concentration).

Following analysis, the second pump 532 (pump #0) flushes the flow cell 548 and sends the flushed contents to the waste bladder 554. This flush can be done with a cleaning solution from the terg tank 558. In some embodiments, the second pump 532 is in fluid communication with the tube 560 (T9) and the terg tank 558 because the valve 559 (V7b) is open. The second pump 532 forces cleaning solution from the terg tank 558 through the open valve 561 and the tube 562 (T7) when the valve 559 is open. The cleaning flush can pass through the flow cell 548, through the second connector 546, through the tube 564 (T5) and the open valve 563 (V2b), and into the waste bladder 554. Following this flush, Subsequently, the first pump 522 (pump #1) can flush the cleaning solution out of the flow cell 548 using saline in drawn from the saline bag 520. This flush pushes saline through the tube 528 (T4), the tube 534 (T3), the flow cell 548, and the tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

When the fluid source is a living entity such as a patient, in between measurements, a low flow of saline (e.g., 1-5 mL/hr) is preferably moved through the patient tube 512 (T1) and into the patient to keep the patient's vessel open (e.g., to establish a keep vessel open, or "KVO" flow). The source of this KVO flow can be the infusion pump 518, the third pump 568 (pump #3), or the first pump 522 (pump #1). In some embodiments, the infusion pump 518 can run continuously throughout the measurement cycle described above. This continuous flow can advantageously avoid any alarms that may be triggered if the infusion pump 518 senses that the flow has stopped or changed in some other way. In some embodiments, when the valve 521 closes to allow pump 522 (pump #1) to withdraw fluid from a fluid source (e.g., a patient), the third pump 568 (pump #3) can withdraw fluid through the connector 570, thus allowing the infusion pump 518 to continue pumping normally as if the fluid path was not blocked by the valve 521. If the measurement cycle is about two minutes long, this withdrawal by the third pump 568 can continue for approximately two minutes. Once the valve 521 is open again, the third pump 568 (pump #3) can reverse and insert the saline back into the system at a low flow rate. Preferably, the time between measurement cycles is longer than the measurement cycle itself (e.g., longer than two minutes). Accordingly, the third pump 568 can insert fluid back into the system at a lower rate than it withdrew that fluid. This can help prevent an alarm by the infusion pump.

Mechanical Fluidics Interface

Figure 6:
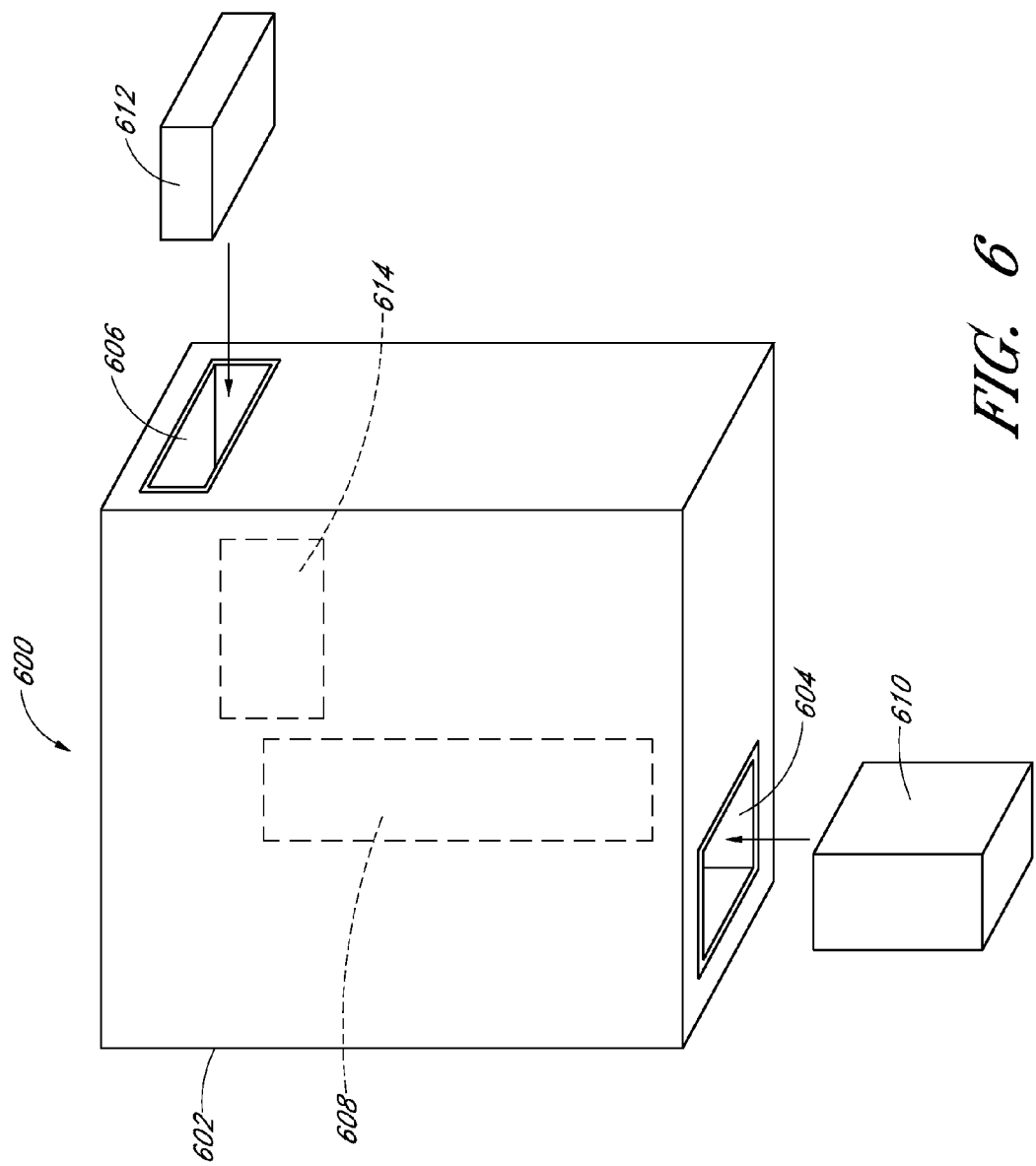
FIG. 6 is an oblique schematic depiction of an embodiment of a modular monitoring device.

FIG. 6 is an oblique schematic depiction of a modular monitoring device 600. The modular monitoring device 600 includes a body portion 602 having receptacles 604, 606. The receptacles 604, 606 include connectors with which disposable cassettes 610, 612 can interface. In some embodiments, portions of the fluidic system that directly contact fluid are incorporated into one or more removable cassettes. For example, a first cassette 610 can be used to store at least a portion of the fluid system 510 described previously, including portions that contact sample fluids, saline, detergent solution, and/or anticoagulant.

In some embodiments, a non-disposable fluidics subsystem 608 is disposed within the body portion 602 of the monitoring device 600. The first cassette 610 can include one or more openings that allow portions of the non-disposable fluidics subsystem 608 to interface with the cassette 610. For example, the non-disposable fluidics subsystem 608 can include one or more pinch valves that are designed to extend through such openings to engage one or more sections of tubing. When the first cassette 610 is inserted into a corresponding first receptacle 604, actuation of the pinch valves can selectively close sections of tubing within the cassette. The non-disposable fluidics subsystem 608 can also include one or more sensors that interface with connectors, tubing sections, or pumps located within the first cassette 610.

In the embodiment shown in FIG. 6, the monitoring device 600 includes an optical system 614 disposed within the body portion 602. The optical system 614 can include a light source and a detector that are adapted to perform measurements on fluids within a flow cell. In some embodiments, the flow cell is disposed within a second cassette 612. The second cassette 612 can include an optical window through which the optical system 614 can shine radiation for measuring properties of a fluid in the flow cell when the cassette is inserted into a corresponding second receptacle 606. The optical system 614 can include other components (some of which may interface with the second cassette 612) such as, for example, a power supply, a centrifuge motor, a filter wheel, and/or a beam splitter.

In some embodiments, the first cassette 610 and the second cassette 612 are adapted to be in fluid communication with each other. For example, the first cassette 610 can include a retractable injector that injects fluids into a flow cell disposed in the second cassette 612. In some embodiments, the injector can be retracted to allow the centrifuge to rotate the flow cell freely. In other embodiments, a fluid communication path can be provided by components disposed within the body portion 602 of the monitoring device 600.

The body portion 602 of the monitoring device 600 can also include one or more connectors for an external battery (not shown). The external battery can serve as a backup emergency power source in the event that a primary emergency power source such as, for example, an internal battery (not shown) is exhausted.

Figure 7:
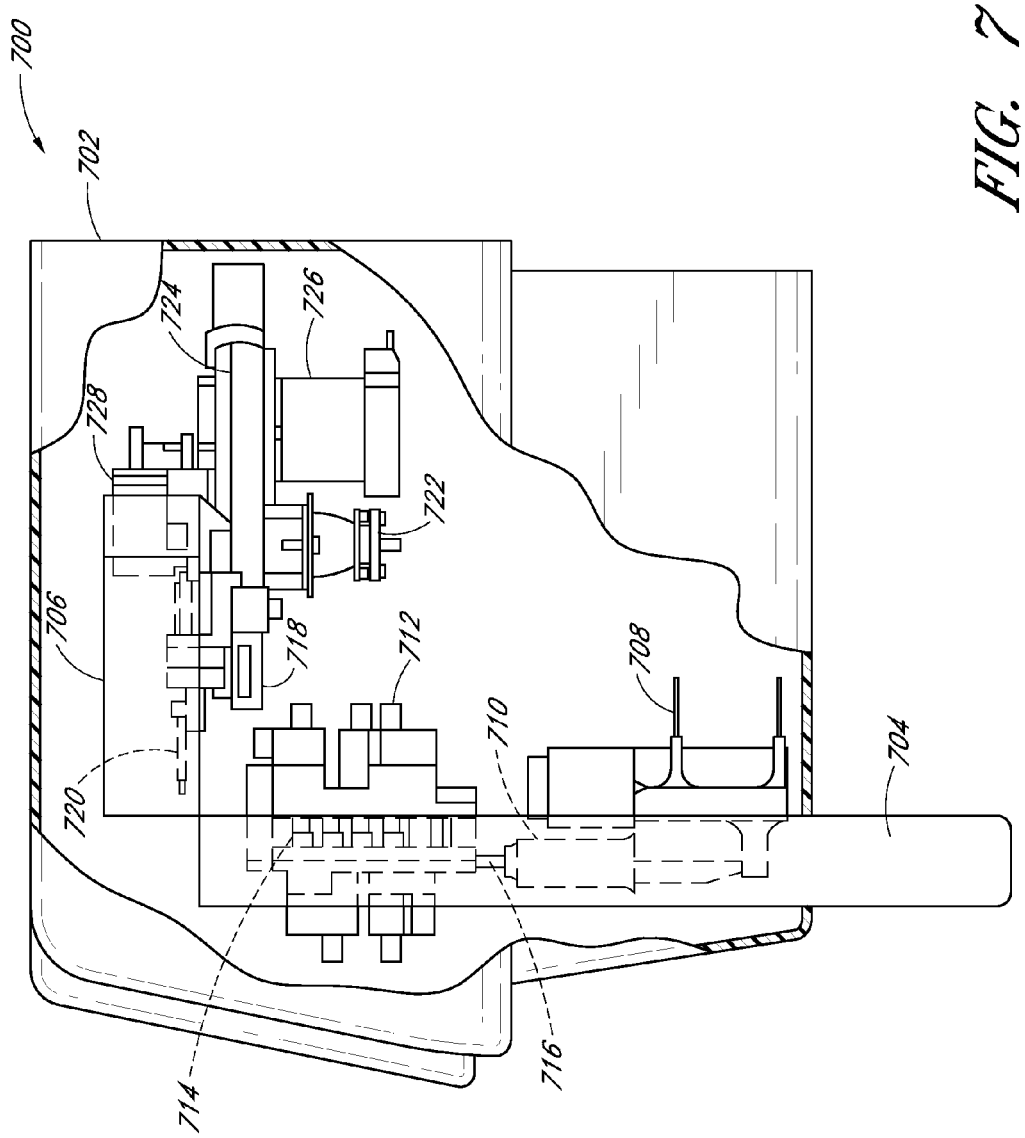
FIG. 7 shows a cut-away side view of an embodiment of a monitoring device.

FIG. 7 shows a cut-away side view of a monitoring device 700 (which can correspond, for example, to the device 102 shown in FIG. 1). The device 700 includes a casing 702 that can include one or more receptacles. Depicted in FIG. 7 are examples of ways in which components of the device 700 mounted within the casing 702 can interact with components of the device 700 disposed within cassettes inserted into the receptacles. Not all components of the device 700 are shown in FIG. 7.

A first cassette 704 having a variety of components is shown inserted into a receptacle formed in the casing 702. A second cassette 706 is also inserted into a receptacle. Components mounted within the cassettes are indicated with dashed lines in FIG. 7, while components mounted within the casing 702 are depicted with solid lines.

In some embodiments, one or more actuators 708 housed within the casing 702 operate syringe pumps 710 located within the first cassette 704. The pumps 710 are connected to sections of tubing 716 that move fluid among various components of the system. The movement of fluid is at least partially controlled by the action of one or more pinch valves 712 positioned within the casing 702. The pinch valves 712 have arms 714 that extend within the first cassette 704. Movement of the arms 714 can constrict a section of tubing 716 in order to create an effective seal.

In some embodiments, the second cassette 706 includes a flow cell 720 that engages a centrifuge motor 718 mounted within the casing 702 of the device 700 when the cassette is inserted into a receptacle. A filter wheel motor 722 disposed within the housing 702 rotates a filter wheel 724 in order to align a filter with a window of the flow cell 720. An optical light path including a light source 726 within the housing 702 routes a beam of infrared light through the filter and the flow cell 720. A detector 728 measures the optical density of the light transmitted through the filter and flow cell 720.

Figure 8:
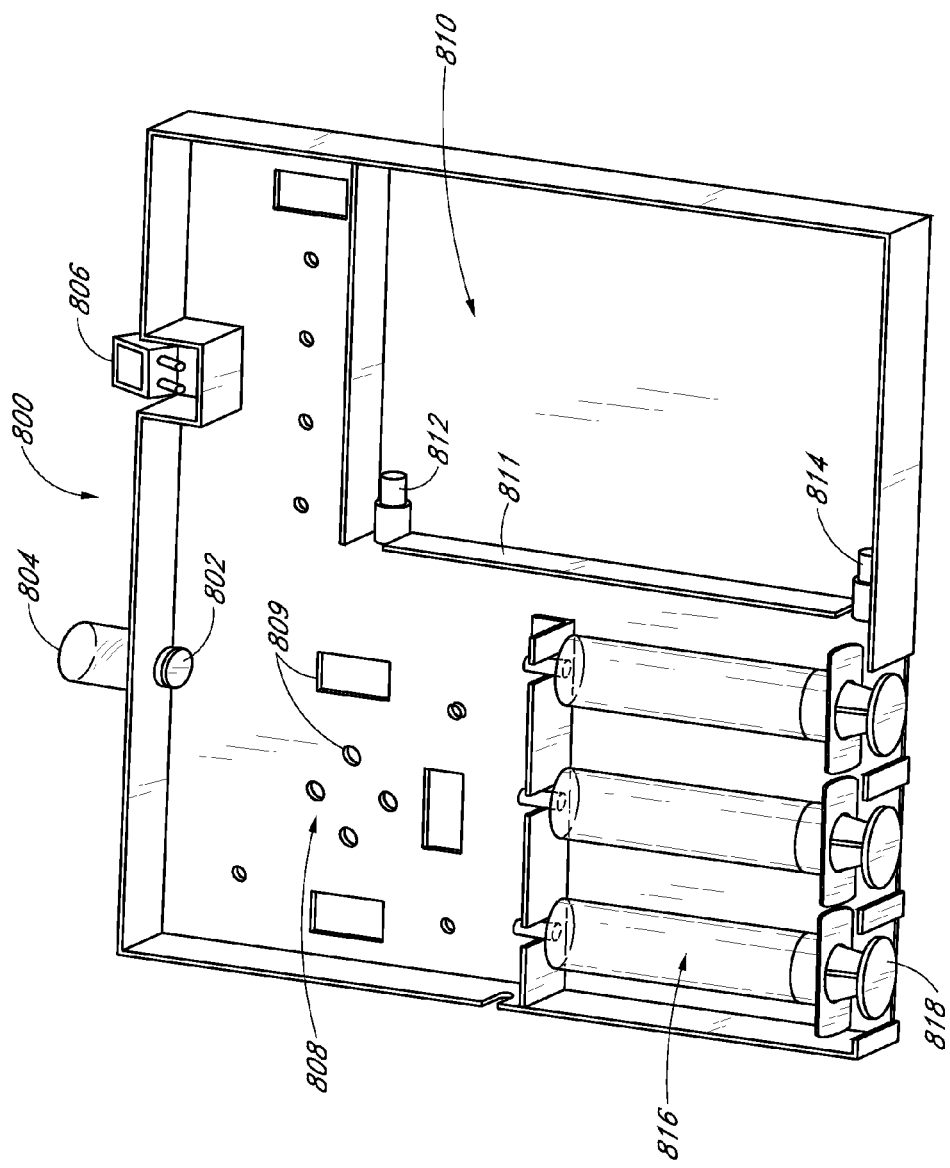
FIG. 8 illustrates an embodiment of a disposable cartridge that can interface with a fluid system.

FIG. 8 illustrates a disposable cartridge 800 that can interface with a fluid system such as the fluid system 510 of FIG. 5. The disposable cartridge 800 can be configured for insertion into a receptacle of the device 700 shown in FIG. 7. In some embodiments, the cartridge 800 includes one or more features that ease insertion of the cartridge 800 into a corresponding receptacle. For example, the cartridge 800 can be shaped so as to promote insertion of the cartridge 800 in the correct orientation. The cartridge 800 can also include labeling or coloring affixed to or integrated with the cartridge's exterior casing that help a handler insert the cartridge 800 into a receptacle properly.

The cartridge 800 can include one or more ports for connecting to material sources. For example, one port 802 can be configured to attach to an anticoagulant source 804. Other ports can be provided to connect to, for example, a saline source, an infusion pump, a sample source, and/or a source of nitrogen gas. The ports can be connected to sections of tubing within the cartridge 800. In some embodiments, the sections of tubing are opaque or covered so that fluids within the tubing cannot be seen.

The cartridge 800 shown in FIG. 8 includes one or more injector needles 806. The injector needles 806 can be configured to inject at least a portion of a sample into a flow cell (not shown). The housing of the cartridge 800 can include a tubing space 808 for one or more sections of tubing. In some embodiments, the body of the cartridge 800 includes one or more apertures 809 through which various components, such as, for example, pinch valves and sensors, can interface with the fluidics contained in the cartridge 800. The sections of tubing found in the tubing space 808 can be aligned with the apertures 809 in order to implement at least some of the functionality shown in the fluid system 510 of FIG. 5.

The cartridge 800 can include a pouch space 810 for storing one or more components of the fluid system 510. For example, one or more pouches and/or bladders can be disposed in the pouch space 810. In some embodiments, a cleaner pouch and a waste bladder are housed in the pouch space 810. The waste bladder can be placed under the cleaner pouch such that, as detergent is removed from the cleaner pouch, the waste bladder has more room to fill. The components placed in the pouch space 810 can also be placed side-by-side or in any other suitable configuration. The pouch space 810 can be isolated from the rest of the cartridge 800 by one or more walls 811. One or more connectors 812, 814 can be formed adjacent to the pouch space 810 to provide communication between components housed in the pouch space 810 and other components of the fluid system 510.

The cartridge 800 can include one or more pumps 816 that facilitate movement of fluid within the fluid system 510. Each of the pumps 816 can be, for example, a syringe pump having a plunger. The plunger can include a portion 818 configured to interface with an actuator housed outside the cartridge 800. For example, the portion 818 of the pump that interfaces with an actuator can be exposed to the exterior of the cartridge 800 housing by one or more apertures in the housing.

In some embodiments, the disposable cartridge 800 is designed for single patient use. The cartridge 800 may also be designed for replacement after a period of operation. For example, in some embodiments, if the cartridge 800 is installed in a continuously operating monitoring device that performs four measurements per hour, the waste bladder may become filled or the detergent in the cleaner pouch depleted after about three days. The cartridge 800 can be replaced before the detergent and waste bladder are exhausted.

The cartridge 800 can be configured for easy replacement. For example, in some embodiments, the cartridge 800 is designed to have an installation time of only several minutes. For example, the cartridge can be designed to be installed in less than about five minutes. During installation, various portions of the fluidics contained in the cartridge 800 can be primed by automatically filling the fluidics with saline. The saline can be mixed with detergent powder from the cleaner pouch in order to create a cleaning solution.

The cartridge 800 can also be designed to have a relatively brief shut down time. For example, the shut down process can be configured to take less than about five minutes. The shut down process can include flushing the patient line; sealing off the insulin pump connection, the saline source connection, and the sample source connection; and taking other steps to decrease the risk that fluids within the used cartridge 800 will leak after disconnection from the monitoring device.

In some embodiments, the cartridge 800 is designed to fit within standard waste containers found in a hospital, such as a standard biohazard container. For example, the cartridge 800 can be less than one foot long, less than one foot wide, and less than two inches thick. In some embodiments, the cartridge 800 is designed to withstand a substantial impact, such as that caused by hitting the ground after a four foot drop, without damage to the housing or internal components. In some embodiments, the cartridge 800 is designed to withstand significant clamping force applied to its casing. For example, the cartridge 800 can be built to withstand five pounds per square inch of force without damage. In some embodiments, the cartridge 800 is non pyrogenic and/or latex free.

Spectroscopy

As described above with reference to FIG. 4, the system 400 comprises the optical system 412 for analysis of a fluid sample. In various embodiments, the optical system 412 comprises one or more optical components including, for example, a spectrometer, a photometer, a reflectometer, or any other suitable device for measuring optical properties of the fluid sample. The optical system 412 may perform one or more optical measurements on the fluid sample including, for example, measurements of transmittance, absorbance, reflectance, scattering, and/or polarization. The optical measurements may be performed in one or more wavelength ranges including, for example, infrared (IR) and/or optical wavelengths. As described with reference to FIG. 4 (and further described below), the measurements from the optical system 412 are communicated to the algorithm processor 416 for analysis. For example, in one embodiment the algorithm processor 416 computes concentration of analyte(s) (and/or interferent(s)) of interest in the fluid sample. Analytes of interest include, e.g., glucose and lactate in whole blood or blood plasma.

Figure 9:
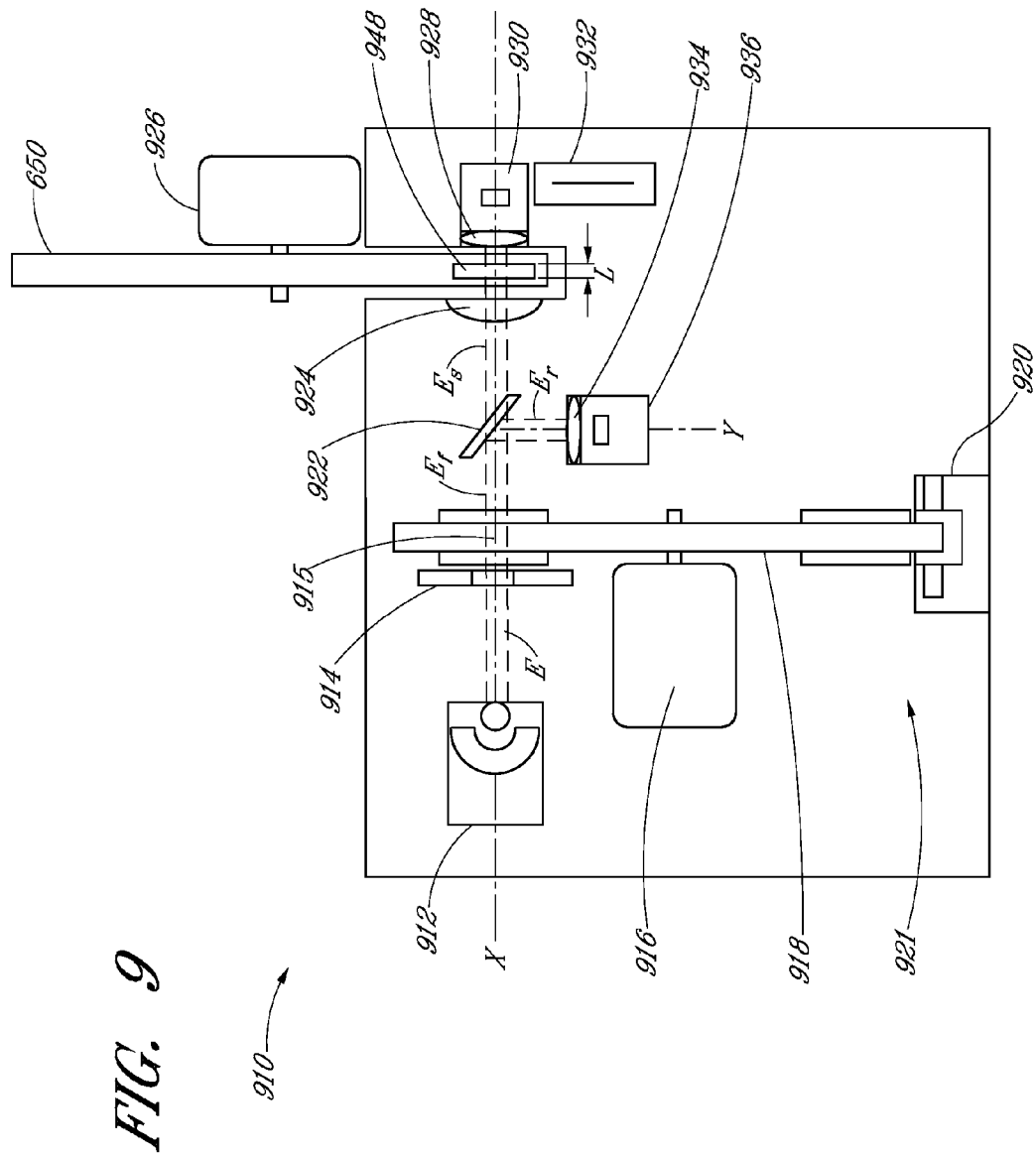
FIG. 9 schematically illustrates an embodiment of an optical system that comprises a spectroscopic analyzer adapted to measure spectra of a fluid sample.

FIG. 9 schematically illustrates an embodiment of the optical system 412 that comprises a spectroscopic analyzer 910 adapted to measure spectra of a fluid sample such as, for example, blood or blood plasma. The analyzer 910 comprises an energy source 912 disposed along an optical axis X of the analyzer 910. When activated, the energy source 912 generates an electromagnetic energy beam E, which advances from the energy source 912 along the optical axis X. In certain embodiments, the energy source 912 comprises an infrared energy source, and the energy beam E comprises an infrared beam. In some embodiments, the infrared energy beam E comprises a mid-infrared energy beam or a near-infrared energy beam. In certain embodiments, the energy beam E may include optical and/or radio frequency wavelengths.

The energy source 912 may comprise a broad-band and/or a narrow-band source of electromagnetic energy. In some embodiments, the energy source 912 comprises optical elements such as, e.g., filters, collimators, lenses, mirrors, etc., that are adapted to produce a desired energy beam E. For example, in some embodiments, the energy beam E is an infrared beam in a wavelength range between about 2 µm and 20 µm. In certain embodiments, the energy beam E comprises an infrared beam in a wavelength range between about 4 µm and 10 µm. In the infrared wavelength range, water generally is the main contributor to the total absorption together with features from absorption of other blood components, particularly in the 6 µm-10 µm range. The 4 µm to 10 µm wavelength band has been found to be advantageous for determining glucose concentration, because glucose has a strong absorption peak structure from about 8.5 µm to 10 µm, whereas most other blood components have a relatively low and flat absorption spectrum in the 8.5 µm to 10 µm range. Two exceptions are water and hemoglobin, which are interferents in this range.

The energy beam E may be temporally modulated to provide increased signal-to-noise ratio (S/N) of the measurements provided by the analyzer 910 as further described below. For example, in some embodiments, the beam E is modulated at a frequency of about 10 Hz or in a range from about 1 Hz to about 30 Hz. A suitable energy source 912 may be an electrically modulated thin-film thermoresistive element such as the HawkEye IR-50 available from Hawkeye Technologies of Milford, Conn.

As depicted in FIG. 9, the energy beam E propagates along the optical axis X and passes through an aperture 914 and a filter 915 thereby providing a filtered energy beam $E_f$. The aperture 914 helps collimate the energy beam E and may include one or more filters adapted to reduce the filtering burden of the filter 915. For example, the aperture 914 may comprise a broadband filter that substantially attenuates beam energy outside a wavelength band between about 4 µm to about 10 µm. The filter 915 may comprise a narrow-band filter that substantially attenuates beam energy having wavelengths outside of a filter passband (which may be tunable or user-selectable in some embodiments). The filter passband may be specified by a half-power bandwidth ("HPBW"). In some embodiments, the filter 915 may have an HPBW in a range from about 0.01 µm to about 1 µm. In one embodiment, the bandwidths are in a range from about 0.1 µm to 0.35 µm. Other filter bandwidths may be used. The filter 915 may comprise a varying-passband filter, an electronically tunable filter, a liquid crystal filter, an interference filter, and/or a gradient filter. In some embodiments, the filter 915 comprises one or a combination of a grating, a prism, a monochrometer, a Fabry-Perot etalon, and/or a polarizer. Other optical elements as known in the art may be utilized as well.

In the embodiment shown in FIG. 9, the analyzer 910 comprises a filter wheel assembly 921 configured to dispose one or more filters 915 along the optical axis X. The filter wheel assembly 921 comprises a filter wheel 918, a filter wheel motor 916, and a position sensor 920. The filter wheel 918 may be substantially circular and have one or more filters 915 or other optical elements (e.g., apertures, gratings, polarizers, etc.) disposed around the circumference of the wheel 918. In some embodiments, the number of filters 915 in the filter wheel 916 may be, for example, 1, 2, 5, 10, 15, 20, 25, or more. The motor 916 is configured to rotate the filter wheel 918 to dispose a desired filter 915 (or other optical element) in the energy beam E so as to produce the filtered beam $E_f$. In some embodiments, the motor 916 comprises a stepper motor. The position sensor 920 determines the angular position of the filter wheel 916, and communicates a corresponding filter wheel position signal to the algorithm processor 416, thereby indicating which filter 915 is in position on the optical axis X. In various embodiments, the position sensor 920 may be a mechanical, optical, and/or magnetic encoder. An alternative to the filter wheel 918 is a linear filter translated by a motor. The linear filter may include an array of separate filters or a single filter with properties that change along a linear dimension.

The filter wheel motor 916 rotates the filter wheel 918 to position the filters 915 in the energy beam E to sequentially vary the wavelengths or the wavelength bands used to analyze the fluid sample. In some embodiments, each individual filter 915 is disposed in the energy beam E for a dwell time during which optical properties in the passband of the filter are measured for the sample. The filter wheel motor 916 then rotates the filter wheel 918 to position another filter 915 in the beam E. In one embodiment, 25 narrow-band filters are used in the filter wheel 918, and the dwell time is about 2 seconds for each filter 915. A set of optical measurements for all the filters can be taken in about 2 minutes, including sampling time and filter wheel movement. In some embodiments, the dwell time may be different for different filters 915, for example, to provide a substantially similar S/N ratio for each filter measurement. Accordingly, the filter wheel assembly 921 functions as a varying-passband filter that allows optical properties of the sample to be analyzed at a number of wavelengths or wavelength bands in a sequential manner.

In certain embodiments of the analyzer 910, the filter wheel 918 includes 25 finite-bandwidth infrared filters having a Gaussian transmission profile and full-width half-maximum (FWHM) bandwidth of 28 $cm^{-1}$ corresponding to a bandwidth that varies from 0.14 μm at 7.08 μm to 0.28 μm at 10 μm. The central wavelength of the filters are, in microns: 7.082, 7.158, 7.241, 7.331, 7.424, 7.513, 7.605, 7.704, 7.800, 7.905, 8.019, 8.150, 8.271, 8.598, 8.718, 8.834, 8.969, 9.099, 9.217, 9.346, 9.461, 9.579, 9.718, 9.862, and 9.990.

With further reference to FIG. 9, the filtered energy beam $E_f$ propagates to a beamsplitter 922 disposed along the optical axis X. The beamsplitter 922 separates the filtered energy beam $E_f$ into a sample beam $E_s$ and a reference beam $E_r$. The reference beam $E_r$ propagates along a minor optical axis Y, which in this embodiment is substantially orthogonal to the optical axis X. The energies in the sample beam $E_s$ and the reference beam $E_r$ may comprise any suitable fraction of the energy in the filtered beam $E_f$. For example, in some embodiments, the sample beam $E_s$ comprises about 80%, and the reference beam $E_r$ comprises about 20%, of the filtered beam energy $E_f$. A reference detector 936 is positioned along the minor optical axis Y. An optical element 934, such as a lens, may be used to focus or collimate the reference beam $E_r$ onto the reference detector 936. The reference detector 936 provides a reference signal, which can be used to monitor fluctuations in the intensity of the energy beam E emitted by the source 912. Such fluctuations may be due to drift effects, aging, wear, or other imperfections in the source 912. The algorithm processor 416 may utilize the reference signal to identify changes in properties of the sample beam $E_s$ that are attributable to changes in the emission from the source 912 and not to the properties of the fluid sample. By so doing, the analyzer 910 may advantageously reduce possible sources of error in the calculated properties of the fluid sample (e.g., concentration). In other embodiments of the analyzer 910, the beamsplitter 922 is not used, and substantially all of the filtered energy beam $E_f$ propagates to the fluid sample.

As illustrated in FIG. 9, the sample beam $E_s$ propagates along the optical axis X, and a relay lens 924 transmits the sample beam $E_s$ into a sample cell 948 so that at least a fraction of the sample beam $E_s$ is transmitted through at least a portion of the fluid sample in the sample cell 948. A sample detector 930 is positioned along the optical axis X to measure the sample beam $E_s$ that has passed through the portion of the fluid sample. An optical element 928, such as a lens, may be used to focus or collimate the sample beam $E_s$ onto the sample detector 930. The sample detector 930 provides a sample signal that can be used by the algorithm processor 416 as part of the sample analysis.

In the embodiment of the analyzer 910 shown in FIG. 9, the sample cell 948 comprises the flow cell 648 located toward the circumference of the centrifuge wheel 650. The flow cell 648 comprises windows that are substantially transmissive to energy in the sample beam $E_s$. For example, in implementations using mid-infrared energy, the windows may comprise calcium fluoride. As described herein with reference to FIG. 5, the flow cell 648 is in fluid communication with an injector system that permits filling the flow cell 648 with a fluid sample (e.g., whole blood) and flushing the flow cell 648 (e.g., with saline or a detergent). The injector system may disconnect after filling the flow cell 648 with the fluid sample to permit free spinning of the centrifuge wheel 650 by centrifuge motor 926. In certain embodiments of the analyzer 910, the fluid sample (e.g., a whole blood sample) is spun at about 7200 rpm for about 2 minutes to separate blood plasma for spectral analysis. In some embodiments, an anti-clotting agent such as heparin may be added to the fluid sample before centrifuging to reduce clotting.

The embodiment of the analyzer 910 illustrated in FIG. 9 advantageously permits direct measurement of the concentration of analytes in the plasma sample rather than by inference of the concentration from measurements of a whole blood sample. An additional advantage is that relatively small volumes of fluid may be spectroscopically analyzed. For example, in certain embodiments the fluid sample volume is between about 1 μL and 80 μL and is about 25 μL in some embodiments. In certain embodiments, the flow cell 648 is disposable and is intended for use with a single patient or for a single measurement.

In certain embodiments, the reference detector 936 and the sample detector 930 comprise broadband pyroelectric detectors. As known in the art, some pyroelectric detectors are sensitive to vibrations. Thus, for example, the output of a pyroelectric infrared detector is the sum of the exposure to infrared radiation and to vibrations of the detector. The sensitivity to vibrations, also known as "microphonics," can introduce a noise component to the measurement of the reference and sample energy beams $E_r$, $E_s$ using some pyroelectric infrared detectors. Because it may be desirable for the analyzer 910 to provide high signal-to-noise ratio measurements, such as, e.g., S/N in excess of 100 dB, some embodiments of the analyzer 910 utilize one or more vibrational noise reduction apparatus or methods. For example, the analyzer 910 may be mechanically isolated so that high S/N spectroscopic measurements can be obtained for vibrations below an acceleration of about 1.5 G.

In some embodiments of the analyzer 910, vibrational noise can be reduced by using a temporally modulated energy source 912 combined with an output filter. In certain embodiments, the energy source 912 is modulated at a known source frequency, and measurements made by the detectors 936 and 930 are filtered using a narrowband filter centered at the source frequency. For example, in one embodiment, the energy output of the source 912 is sinusoidally modulated at 10 Hz, and outputs of the detectors 936 and 930 are filtered using a narrow bandpass filter of less than about 1 Hz centered at 10 Hz. Accordingly, microphonic signals that are not at 10 Hz are significantly attenuated. In some embodiments, the modulation depth of the energy beam E may be greater than 50% such as, for example, 80%. The duty cycle of the beam may be between about 30% and 70%. The temporal modulation may be sinusoidal or any other waveform. In embodiments utilizing temporally modulated energy sources, detector output may be filtered using a synchronous demodulator and digital filter. The demodulator and filter are software components that may be digitally implemented in a processor such as the algorithm processor 416. Synchronous demodulators, coupled with low pass filters, are often referred to as "lock in amplifiers."

The analyzer 910 may also include a vibration sensor 932 (e.g., one or more accelerometers) disposed near one (or both) of the detectors 936 and 930. The output of the vibration sensor 932 is monitored, and suitable actions are taken if the measured vibration exceeds a vibration threshold. For example, in some embodiments, if the vibration sensor 932 detects above-threshold vibrations, the system discards any ongoing measurement and "holds off" on performing further measurements until the vibrations drop below the threshold. Discarded measurements may be repeated after the vibrations drop below the vibration threshold. In some embodiments, if the duration of the "hold off" is sufficiently long, the fluid in the sample cell 930 is flushed, and a new fluid sample is delivered to the cell 930 for measurement. The vibration threshold may be selected so that the error in analyte measurement is at an acceptable level for vibrations below the threshold. In some embodiments, the threshold corresponds to an error in glucose concentration of 5 mg/dL. The vibration threshold may be determined individually for each filter 915.

Certain embodiments of the analyzer 910 include a temperature system (not shown in FIG. 9) for monitoring and/or regulating the temperature of system components (such as the detectors 936, 930) and/or the fluid sample. Such a temperature system may include temperature sensors, thermoelectrical heat pumps (e.g., a Peltier device), and/or thermistors, as well as a control system for monitoring and/or regulating temperature. In some embodiments, the control system comprises a proportional-plus-integral-plus-derivative (PID) control. For example, in certain embodiments, the temperature system is used to regulate the temperature of the detectors 930, 936 to a desired operating temperature, such as 35 degrees Celsius.

The analyzer 910 illustrated in FIG. 9 can be used to determine optical properties of a substance in the sample cell 948. The substance may include whole blood, plasma, saline, water, air or other substances. In some embodiments, the optical properties include measurements of an absorbance, transmittance, and/or optical density in the wavelength passbands of some or all of the filters 915 disposed in the filter wheel 918. As described above, a measurement cycle comprises disposing one or more filters 915 in the energy beam E for a dwell time and measuring a reference signal with the reference detector 936 and a sample signal with the sample detector 930. The number of filters 915 used in the measurement cycle will be denoted by N, and each filter 915 passes energy in a passband around a center wavelength $\lambda_i$, where i is an index ranging over the number of filters (e.g., from 1 to N). The set of optical measurements from the sample detector 936 in the passbands of the N filters 915 provide a wavelength-dependent spectrum of the substance in the sample cell 948. The spectrum will be denoted by $C_s(\lambda_i)$, where $C_s$ may be a transmittance, absorbance, optical density, or some other measure of an optical property of the substance. In some embodiments, the spectrum is normalized with respect to one or more of the reference signals measured by the reference detector 930 and/or with respect to spectra of a reference substance (e.g., air or saline). The measured spectra are communicated to the algorithm processor 416 for calculation of the concentration of the analyte(s) of interest in the fluid sample.

In certain embodiments, the analyzer 910 performs spectroscopic measurements on the fluid sample (known as a "wet" reading) and on one or more reference samples. For example, an "air" reading occurs when the sample detector 936 measures the sample signal without the sample cell 948 in place along the optical axis X. A "water" or "saline" reading occurs when the sample cell 948 is filled with water or saline, respectively. The algorithm processor 416 may be programmed to calculate analyte concentration using a combination of these spectral measurements.

In some embodiments, a pathlength corrected spectrum is calculated using wet, air, and reference readings. For example, the transmittance at wavelength $\lambda_i$, denoted by $T_i$, may be calculated according to $T_i=(S_i(\text{wet})/R_i(\text{wet}))/(S_i(\text{air})/R_i(\text{air}))$, where $S_i$ denotes the sample signal from the sample detector 936 and $R_i$ denotes the corresponding reference signal from the reference detector 930. In certain embodiments, the algorithm processor 416 calculates the optical density, $OD_i$, as a logarithm of the transmittance, e.g., according to $OD_i=-\text{Log}(T_i)$. In one implementation, the analyzer 910 takes a set of wet readings in each of the N filter passbands and then takes a set of air readings in each of the N filter passbands. In other embodiments, the analyzer 910 may take an air reading before (or after) the corresponding wet reading.

The optical density $OD_i$ is the product of the absorption coefficient at wavelength $\lambda_i$, $\alpha_i$, times the pathlength L over which the sample energy beam $E_s$ interacts with the substance in the sample chamber 948, e.g., $OD_i=\alpha_i L$. The absorption coefficient $\alpha_i$ of a substance may be written as the product of an absorptivity per mole times a molar concentration of the substance. FIG. 9 schematically illustrates the pathlength L of the sample cell 948. The pathlength L may be determined from spectral measurements made when the sample cell 948 is filled with a reference substance. For example, because the absorption coefficient for water (or saline) is known, one or more water (or saline) readings can be used to determine the pathlength L from measurements of the transmittance (or optical density) through the cell 948. In some embodiments, several readings are taken in different wavelength passbands, and a curve-fitting procedure is used to estimate a best-fit pathlength L. The pathlength L may be estimated using other methods including, for example, measuring interference fringes of light passing through an empty sample cell 948.

The pathlength L may be used to determine the absorption coefficients of the fluid sample at each wavelength. Molar concentration of an analyte of interest can be determined from the absorption coefficient and the known molar absorptivity of the analyte. In one embodiment, a sample measurement cycle comprises a saline reading (at one or more wavelengths), a set of N wet readings, followed by a set of N air readings. As discussed above, the sample measurement cycle can be performed in about 2 minutes when the filter dwell times are about 2 seconds. After the sample measurement cycle is completed, a detergent cleaner may be flushed through the flow cell 648 to reduce buildup of organic matter (e.g., proteins) on the windows of the flow cell 648. The detergent is then flushed to a waste bladder.

In some embodiments, the system stores information related to the spectral measurements so that the information is readily available for recall by a user. The stored information may include wavelength-dependent spectral measurements (including fluid sample, air, and/or saline readings), computed analyte values, system temperatures and electrical properties (e.g., voltages and currents), and any other data related to use of the system (e.g., system alerts, vibration readings, S/N ratios, etc.). The stored information may be retained in the system for a time period such as, for example, 30 days. After this time period, the stored information may be communicated to an archival data storage system and then deleted from the system. In certain embodiments, the stored information is communicated to the archival data storage system via wired or wireless methods, e.g., over a hospital information system (HIS).

Algorithm

The algorithm processor 416 (FIG. 4) (or any other suitable processor) may be configured to receive from the analyzer 910 the wavelength-dependent optical measurements of the fluid sample. In some embodiments, the optical densities $OD_i$ in each of the N filter passbands centered around wavelengths $\lambda_i$ are communicated to the processor 416, which analyzes the optical densities to measure and quantify one or more analytes in the presence of interferents. Interferents can comprise components of a material sample being analyzed for an analyte, where the presence of the interferent affects the quantification of the analyte. Thus, for example, in the spectroscopic analysis of a sample to determine an analyte concentration, an interferent could be a compound having spectroscopic features that overlap with those of the analyte. The presence of such an interferent can introduce errors in the quantification of the analyte. More specifically, the presence of interferents can affect the sensitivity of a measurement technique to the concentration of analytes of interest in a material sample, especially when the system is calibrated in the absence of, or with an unknown amount of, the interferent.

Independently of or in combination with the attributes of interferents described above, interferents can be classified as being endogenous (i.e., originating within the body) or exogenous (i.e., introduced from or produced outside the body). As an example of these classes of interferents, consider the analysis of a blood sample (or a blood component sample or a blood plasma sample) for the analyte glucose. Endogenous interferents include those blood components having origins within the body that affect the quantification of glucose, and may include water, hemoglobin, blood cells, and any other component that naturally occurs in blood. Exogenous interferents include those blood components having origins outside of the body that affect the quantification of glucose, and can include items administered to a person, such as medicaments, drugs, foods or herbs, whether administered orally, intravenously, topically, etc.

Independently of or in combination with the attributes of interferents described above, interferents can comprise components which are possibly, but not necessarily, present in the sample type under analysis. In the example of analyzing samples of blood or blood plasma drawn from patients who are receiving medical treatment, a medicament such as acetaminophen is possibly, but not necessarily, present in this sample type. In contrast, water is necessarily present in such blood or plasma samples.

Figure 10:
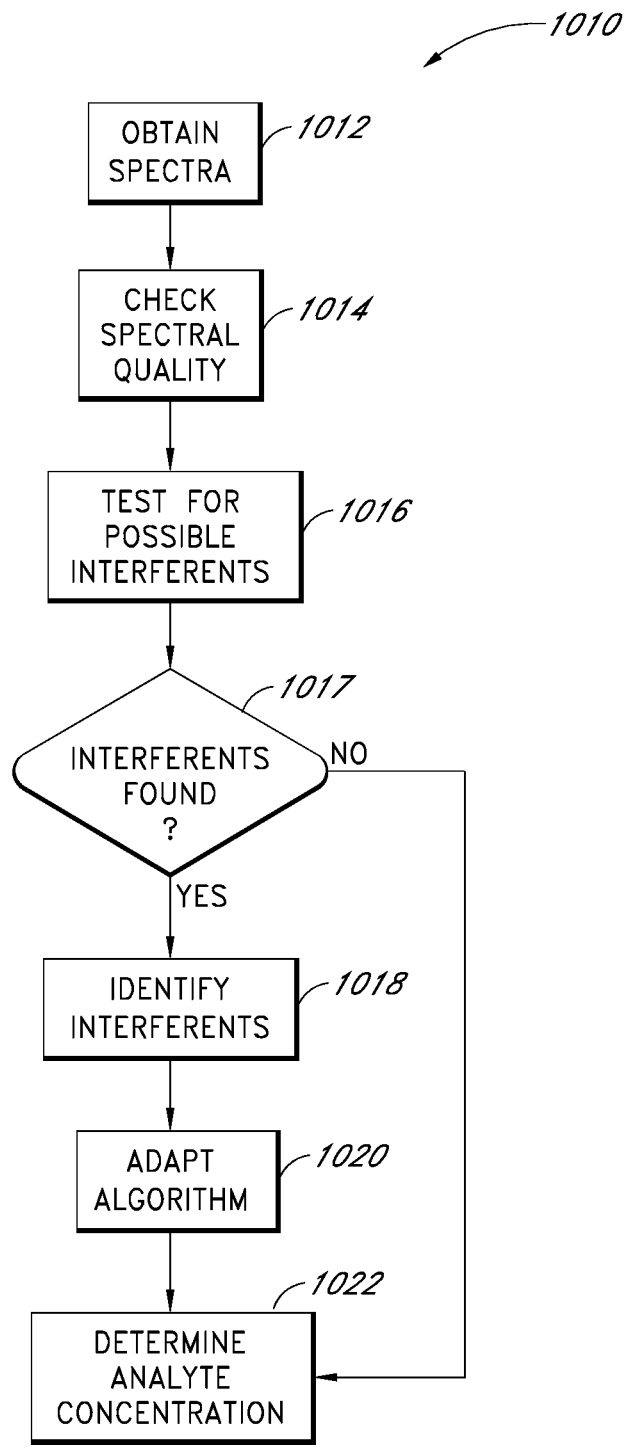
FIG. 10 is a flowchart that schematically illustrates an embodiment of a spectroscopic method for determining the concentration of an analyte of interest in a fluid sample.

FIG. 10 is a flowchart that schematically illustrates an embodiment of a spectroscopic method 1010 for determining the concentration of an analyte of interest in a fluid sample in the presence of one or more possible interferents. In block 1012, spectral measurements of the fluid sample are obtained. For example, as described above with reference to FIG. 9, the analyzer 910 may be used to obtain optical measurements $Cs(\lambda_i)$ of the fluid sample in a number N of filter passbands centered around wavelengths $\lambda_i$. In block 1014, quality of the spectral measurements is determined regardless of the concentration of the analyte of interest of the presence of possible interferents. In some embodiments, one or more of poor quality spectral measurements $Cs(\lambda_i)$ may be rejected (e.g., as having a S/N ratio that is too low), and the method 1010 performed on the remaining, sufficiently high-quality measurements. In other embodiments, additional spectral measurements of the fluid sample are obtained to replace one or more of the poor quality measurements.

In block 1016, the spectral measurements are tested to determine the possible presence of interferents. For example, the system may utilize spectroscopic signatures of possible interferents to test for their presence. In block 1017, if the test determines that no interferents are present or that any possible interferents, if present, are at concentrations below suitable thresholds, the method 1010 proceeds to block 1022 in which analyte concentration is determined. In one embodiment, analyte concentration is determined using a hybrid linear algorithm (HLA) in which analyte concentration is estimated from measured spectra using one or more calibration coefficients and an offset. If in block 1017 the test determines that one or more interferents are present at concentrations above threshold, then, in block 1018, the above-threshold interferents are identified. The method 1010 proceeds to block 1020 in which the analyte concentration algorithm is adapted to account for the presence of one or more of the identified interferents. For example, in embodiments using HLA, the calibration coefficients may be adjusted to compensate for the presence of some or all of the identified interferents. The method 1010 proceeds to block 1022 in which analyte concentration is determined as further described below.

Certain disclosed analysis methods are particularly effective if each analyte and interferent has a characteristic signature in the measurement (e.g., a characteristic spectroscopic feature), and if the measurement is approximately affine (e.g., includes a linear term and an offset) with respect to the concentration of each analyte and interferent. In such methods, a calibration process is used to determine a set of one or more calibration coefficients and one or more optional offset values that permits the quantitative estimation of an analyte. For example, the calibration coefficients and the offsets may be used to calculate an analyte concentration from spectroscopic measurements of a material sample (e.g., the concentration of glucose in blood plasma). In some of these methods, the concentration of the analyte is estimated by multiplying the calibration coefficient by a measurement value (e.g., an optical density) to estimate the concentration of the analyte. Both the calibration coefficient and measurement can comprise arrays of numbers. For example, in some embodiments, the measurement comprises the spectra $C_s(\lambda_i)$ measured at the wavelengths $\lambda_i$, and the calibration coefficient and optional offset comprise an array of values corresponding to each wavelength $\lambda_i$. As described with reference to blocks 1017-1020 of FIG. 10, in some embodiments a hybrid linear algorithm (HLA) is used to estimate analyte concentration in the presence of a set of interferents, while retaining a high degree of sensitivity to the desired analyte. The data used to accommodate the random set of interferents may include (a) signatures of each of the members of the family of potential additional substances and (b) the typical quantitative level at which each additional substance, if present, is likely to appear. As described with reference to block 1020, in some embodiments, the calibration constant (and optional offset) are adjusted to minimize or reduce the sensitivity of the calibration to the presence of interferents that are identified as possibly being present in the fluid sample.

In one embodiment, the analyte analysis method uses a set of training spectra each having known analyte concentration(s) and produces a calibration that minimizes the variation in estimated analyte concentration with interferent concentration. The resulting calibration coefficient measures sensitivity of the measurement to analyte concentration(s) and, on average, is not sensitive to interferent concentrations. The training spectra need not include a spectrum from the individual whose analyte concentration is to be determined. That is, the term "training" when used in reference to the disclosed methods does not require training using measurements from the individual whose analyte concentration will be estimated (e.g., by analyzing a bodily fluid sample drawn from the individual).

Several terms are used herein to describe the analyte analysis process. The term "Sample Population" is a broad term and includes, without limitation, a large number of samples having measurements that are used in the computation of a calibration—in other words, used to train the method of generating a calibration. For an embodiment involving the spectroscopic determination of glucose concentration, the Sample Population measurements can each include a spectrum (analysis measurement) and a glucose concentration (analyte measurement). In one embodiment, the Sample Population measurements are stored in a database, referred to herein as a "Population Database."

The Sample Population may or may not be derived from measurements of material samples that contain interferents to the measurement of the analyte(s) of interest. One distinction made herein between different interferents is based on whether the interferent is present in both the Sample Population and the sample being measured, or only in the sample. As used herein, the term "Type-A interferent" refers to an interferent that is present in both the Sample Population and in the material sample being measured to determine an analyte concentration. In certain methods it is assumed that the Sample Population includes only interferents that are endogenous, and does not include any exogenous interferents, and thus Type-A interferents are endogenous. The number of Type-A interferents depends on the measurement and analyte(s) of interest, and may number, in general, from zero to a very large number (e.g., greater than 300). The material sample being measured, for example a fluid sample in the sample cell 948, may also include interferents that are not present in the Sample Population.

As used herein, the term "Type-B interferent" refers to an interferent that is either: 1) not found in the Sample Population but that is found in the material sample being measured (e.g., an exogenous interferent), or 2) is found naturally in the Sample Population, but is at abnormally high concentrations in the material sample (e.g., an endogenous interferent). Examples of a Type-B exogenous interferent may include medications, and examples of Type-B endogenous interferents may include urea in persons suffering from renal failure. For example, in mid-infrared spectroscopic absorption measurements of glucose in blood (or blood plasma), water is present in all fluid samples, and is thus a Type-A interferent. For a Sample Population made up of individuals who are not taking intravenous drugs, and a material sample taken from a hospital patient who is being administered a selected intravenous drug, the selected drug is a Type-B interferent. In addition to components naturally found in the blood, the ingestion or injection of some medicines or illicit drugs can result in very high and rapidly changing concentrations of exogenous interferents.

In some embodiment, a list of one or more possible Type-B Interferents is referred to herein as forming a "Library of Interferents," and each interferent in the library is referred to as a "Library Interferent." The Library Interferents include exogenous interferents and endogenous interferents that may be present in a material sample due, for example, to a medical condition causing abnormally high concentrations of the endogenous interferent.

Figure 11:
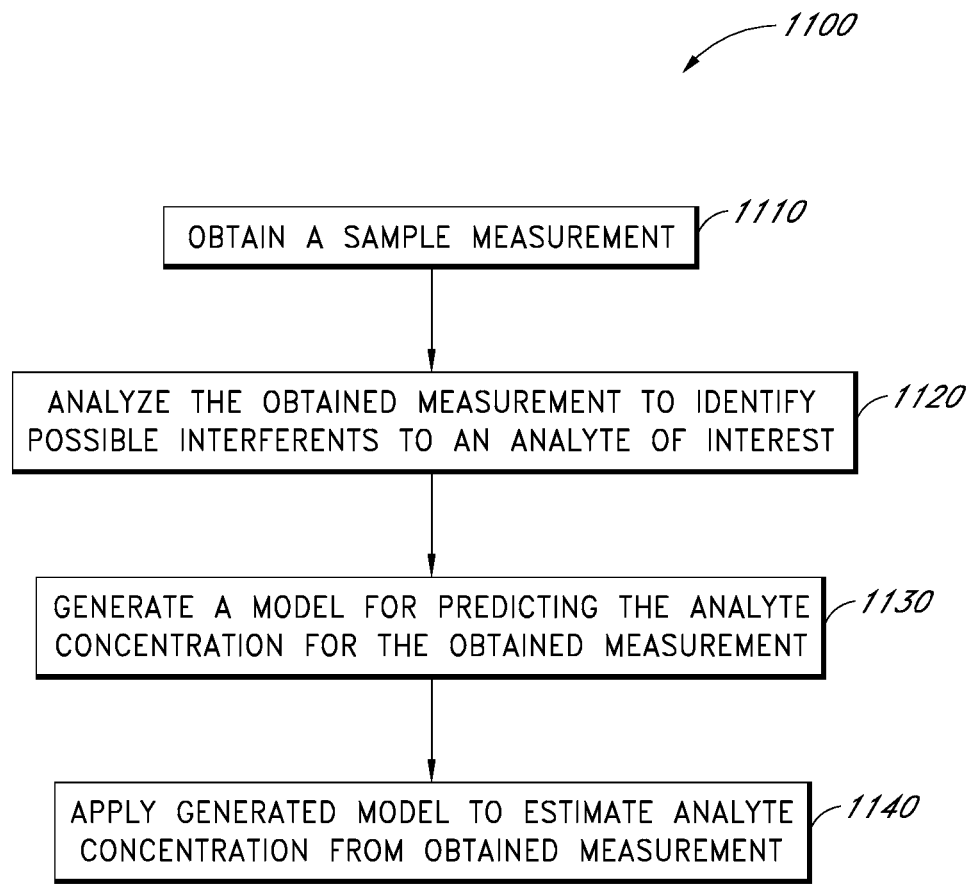
FIG. 11 is a flowchart that schematically illustrates an embodiment of a method for estimating the concentration of an analyte in the presence of interferents.

FIG. 11 is a flowchart that schematically illustrates an embodiment of a method 1100 for estimating the concentration of an analyte in the presence of interferents. In block 1110, a measurement of a sample is obtained, and in block 1120 data relating to the obtained measurement is analyzed to identify possible interferents to the analyte. In block 1130, a model is generated for predicting the analyte concentration in the presence of the identified possible interferents, and in block 1140 the model is used to estimate the analyte concentration in the sample from the measurement. In certain embodiments of the method 1100, the model generated in block 1130 is selected to reduce or minimize the effect of identified interferents that are not present in a general population of which the sample is a member.

An example embodiment of the method 1100 of FIG. 11 for the determination of an analyte (e.g., glucose) in a blood sample will now be described. This example embodiment is intended to illustrate various aspects of the method 1100 but is not intended as a limitation on the scope of the method 1100 or on the range of possible analytes. In this example, the sample measurement in block 1110 is an absorption spectrum, $Cs(\lambda_i)$, of a measurement sample S that has, in general, one analyte of interest, glucose, and one or more interferents. As described with reference to FIG. 9, the absorption spectrum may comprise the set of optical densities $OD_i$ measured by the analyzer 910. In general, the sample S includes Type-A interferents, at concentrations preferably within the range of those found in the Sample Population.

In block 1120, a statistical comparison of the absorption spectrum of the sample S with a spectrum of the Sample Population and combinations of individual Library Interferent spectra is performed. The statistical comparison provides a list of Library Interferents that are possibly contained in sample S and may include either no Library Interferents or one or more Library Interferents. In this example, in block 1130, a set of spectra are generated using the spectra of the Sample Population and their respective known analyte concentrations and known spectra of the Library Interferents identified in block 1120. In block 1130, the generated spectra are used to calculate a calibration coefficient $\kappa(\lambda_i)$ that can be used with the sample measurements $Cs(\lambda_i)$ to provide an estimate of the analyte concentration, $g_{est}$. In block 1140, the estimated analyte concentration is determined. For example, in some embodiments of HLA, the estimated analyte concentration is calculated according to a linear formula: $g_{est} = \kappa(\lambda_i) \cdot C_x(\lambda_i)$. Because the absorption measurements and calibration coefficients may represent arrays of numbers, the multiplication operation indicated in the preceding formula may comprise an inner product or a matrix product. In some embodiments, the calibration coefficient is determined so as to have reduced or minimal sensitivity to the presence of the identified Library Interferents.

Figure 12:
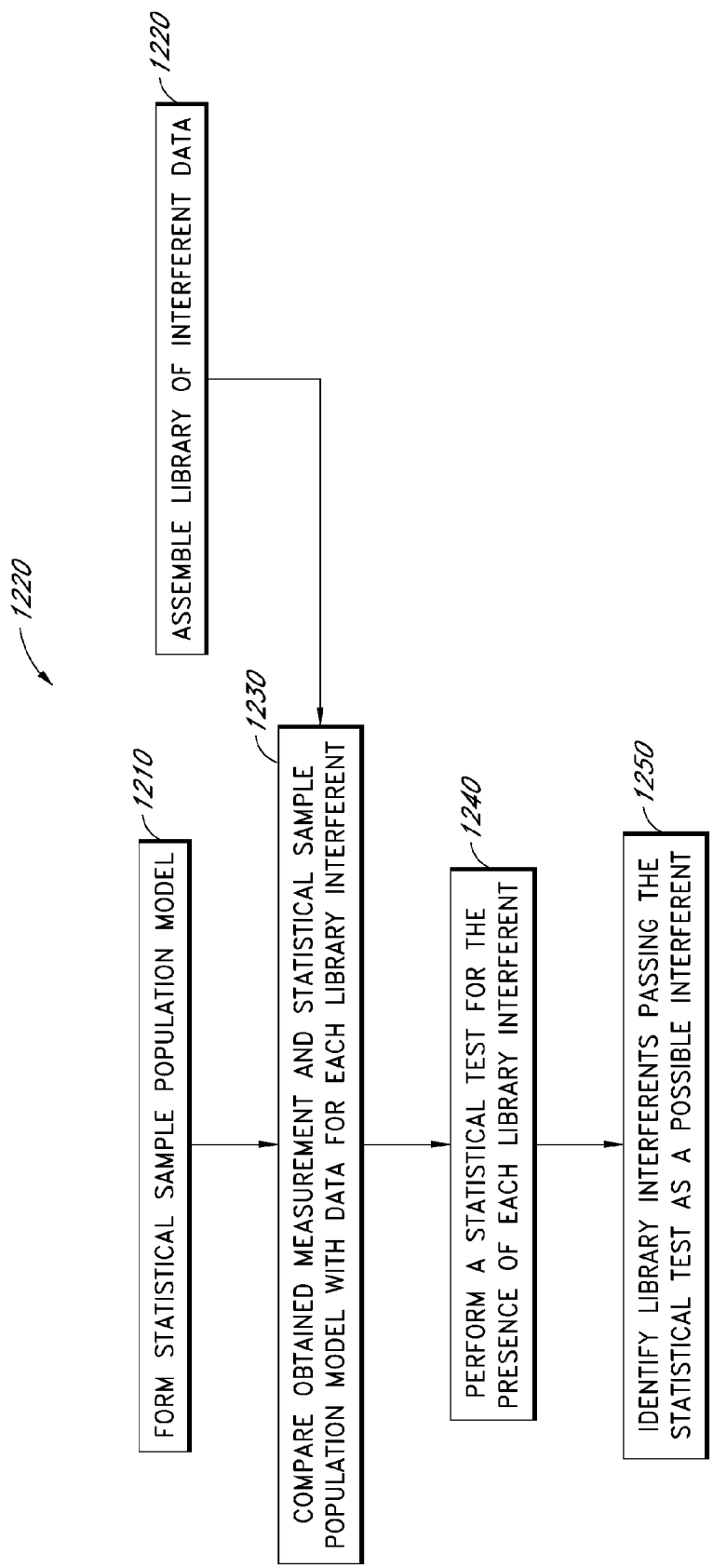
FIG. 12 is a flowchart that schematically illustrates an embodiment of a method for performing a statistical comparison of the absorption spectrum of a sample with the spectrum of a sample population and combinations of individual library interferent spectra.

An example embodiment of block 1120 of the method 1100 will now be described with reference to FIG. 12. In this example, block 1120 includes forming a statistical Sample Population model (block 1210), assembling a library of interferent data (block 1220), comparing the obtained measurement and statistical Sample Population model with data for each interferent from an interferent library (block 1230), performing a statistical test for the presence of each interferent from the interferent library (block 1240), and identifying possible interferents that pass the statistical test (block 1250). The acts of block 1220 can be performed once or can be updated as necessary. The acts of blocks 1230, 1240, and 1250 can either be performed sequentially for all Library Interferents or can be repeated sequentially for each interferent.

In this example, in block 1210, a Sample Population Database is formed that includes a statistically large Sample Population of individual spectra taken over the same wavelength range as the sample spectrum, $C_s(\lambda_i)$. The Database also includes an analyte concentration corresponding to each spectrum. For example, if there are P Sample Population spectra, then the spectra in the Database can be represented as $C=\{C_1, C_2, \ldots, C_P\}$, and the analyte concentration corresponding to each spectrum can be represented as $g=\{g_1, g_2, \ldots, g_P\}$. In some embodiments, the Sample Population does not have any of the Library Interferents present, and the material sample has interferents contained in the Sample Population and one or more of the Library Interferents. Stated in terms of Type-A and Type-B interferents, the Sample Population has Type-A interferents, and the material sample has Type-A and may have Type-B interferents.

In some embodiments of block 1210, the statistical sample model comprises a mean spectrum and a covariance matrix calculated for the Sample Population. For example, if each spectrum measured at N wavelengths $\lambda_i$ is represented by an N×1 array, C, then the mean spectrum, $\mu$, is an N×1 array having values at each wavelength averaged over the range of spectra in the Sample Population. The covariance matrix, V, is calculated as the expected value of the deviation between C and $\mu$ and can be written as $V=E((C-\mu)(C-\mu)^T)$, where $E(\cdot)$ represents the expected value and the superscript T denotes transpose. In other embodiments, additional statistical parameters may be included in the statistical model of the Sample Population spectra.

Additionally, a Library of Interferents may be assembled in block 1220. A number of possible interferents can be identified, for example, as a list of possible medications or foods that might be ingested by the population of patients at issue. Spectra of these interferents can be obtained, and a range of expected interferent concentrations in the blood, or other expected sample material, can be estimated. In certain embodiments, the Library of Interferents includes, for each of "M" interferents, the absorption spectrum of each interferent, $IF=\{IF_1, IF_2, \ldots IFM\}$, and a maximum concentration for each interferent, $Tmax=\{Tmax_1, Tmax_2, \ldots, Tmax_M\}$. Information in the Library may be assembled once and accessed as needed. For example, the Library and the statistical model of the Sample Population may be stored in a storage device associated with the algorithm processor 416 (FIG. 4).

Continuing in block 1230, the obtained measurement data (e.g., the sample spectrum) and the statistical Sample Population model (e.g., the mean spectrum and the covariance matrix) are compared with data for each interferent from the Library of Interferents in order to determine the presence of possible interferents in the sample (block 1240). In some embodiments, the statistical test for the presence of an interferent comprises the following actions. The measured spectrum of the fluid sample, $C_s$, is modified for each interferent of the library by analytically subtracting, wavelength-by-wavelength, the spectrum of the interferent. For any of the M interferents in the Library, having an absorption spectrum per unit of interferent concentration, IF, the modified spectrum is given by $C'_s(T)=C_s-IF\,T$, where T is the interferent concentration. In some embodiments, the interferent concentration is assumed to be in a range from a minimum value, Tmin, to a maximum value, Tmax. The value of Tmin may be zero or, alternatively, be a value between zero and Tmax, such as some fraction of Tmax.

In certain embodiments, the statistical test for determining the presence of possible interferents in block 1240 further comprises determining a Mahalanobis distance (MD) between the modified spectrum $C'_s(T)$ and the statistical model $(\mu, V)$ of the Sample Population. The Mahalanobis distance can be calculated from $$MD^2(C_s-IF\,T,\mu;\rho_s)=(C'_s(T)-\mu)^T V^{-1}(C'_s(T)-\mu). \qquad \text{Eq. (1)}$$

The value of $MD^2$ found from Eq. (1) is referred to herein as the "squared Mahalanobis distance" or the "$MD^2$ score." The $MD^2$ score is used in various embodiments of the statistical test for determining the presence of an interferent.

In block 1250, a list of possible interferents may be identified as the particular Library Interferents that pass one or more statistical tests for being present in the sample. One or more tests may be used, alone or in combination, to identify the possible interferents. For example, if a statistical test indicates that the interferent is present in negative concentrations, then this non-physical result is used to exclude the possible interferent from the list of possible interferents. In some embodiments, only the single most probable interferent is included on the list.

In one test embodiment, for each interferent, the concentration T is varied from Tmin to Tmax (e.g., evaluate $C'_s(T)$ over a range of values of T in Eq. (1)). If the minimum value of MD (or $MD^2$) in this interval is below a minimum threshold, then the test indicates the probable presence of the interferent in the sample. In some embodiments, the minimum threshold $MD^2$ is chosen relative to quantiles of a $\chi^2$ random variable having N degrees of freedom, where N is the number of wavelengths in the spectrum $C_s$. In some embodiments, the 95% quantile is used as the minimum threshold.

In another test embodiment, if the $MD^2$ score is above a maximum threshold, then it is probable that the interferent is not actually present or is not present in a large enough concentration to modify the analyte concentration estimate. The maximum threshold generally is empirically determined. In one embodiment, it is found that a maximum threshold value is in a range from about 50 to about 200.

Another test embodiment includes calculating a probability density that combines a range of probable interferent concentrations and the $MD^2$ score for that interferent. For interferents that are not indicated as being present at negative concentrations and that do not have an $MD^2$ score above the maximum threshold, the probability density $\rho(T)$ is computed, which is given by the product:

$$\rho(T)=\rho_{\chi^2 N}(MD^2(C_s-IF\,T))\rho_T(T), \qquad \text{Eq. (2)}$$

The right-hand-side of Eq. (2) is the product of two probability densities: (1) the $\chi^2$ distribution with N degrees of freedom (where N is the number of wavelengths present in the spectral measurements), evaluated at the Mahalanobis score for the difference spectrum $C_s-IF\,T$, and (2) the distribution of concentrations T for the interferent. In some embodiments, interferent concentration is assumed to have a log-normal distribution with a value of 95% at the assumed maximum interferent concentration in the fluid and a standard deviation of one half the mean.

An integral of $\rho(T)$ is then computed over a range of possible concentrations T, for example from 0 to infinity, or a smaller range, such as from $T_{MIN}=\frac{1}{2}T_{OPT}$ to $T_{MAX}=2\,T_{OPT}$, to give a "raw probably score" (RPS) for the interferent. The RPS is then compared to a minimum value $(P_{min})$. Possible interferents are identified as interferents having an RPS greater than $P_{min}$. Possible interferents are denoted herein with the variable ξ. In some embodiments, the value of $P_{min}$ is empirically determined from an analysis of the measurements. For example, a value of 0.70 may result in a single possible interferent (a "single interferent identification") and a value of 0.3 may result in three possible interferents (a multiple interferent identification).

Accordingly, in block 1250, one or more of the above statistical tests (or other tests as known in the art) are used to determine a list of possible interferents ξ that may be present in the fluid sample. In some embodiments, the list of possible interferents includes only the single most probable interferent. In other embodiments, the list of possible interferents ξ may include each of the interferents in the Library of Interferents.

Figure 13:
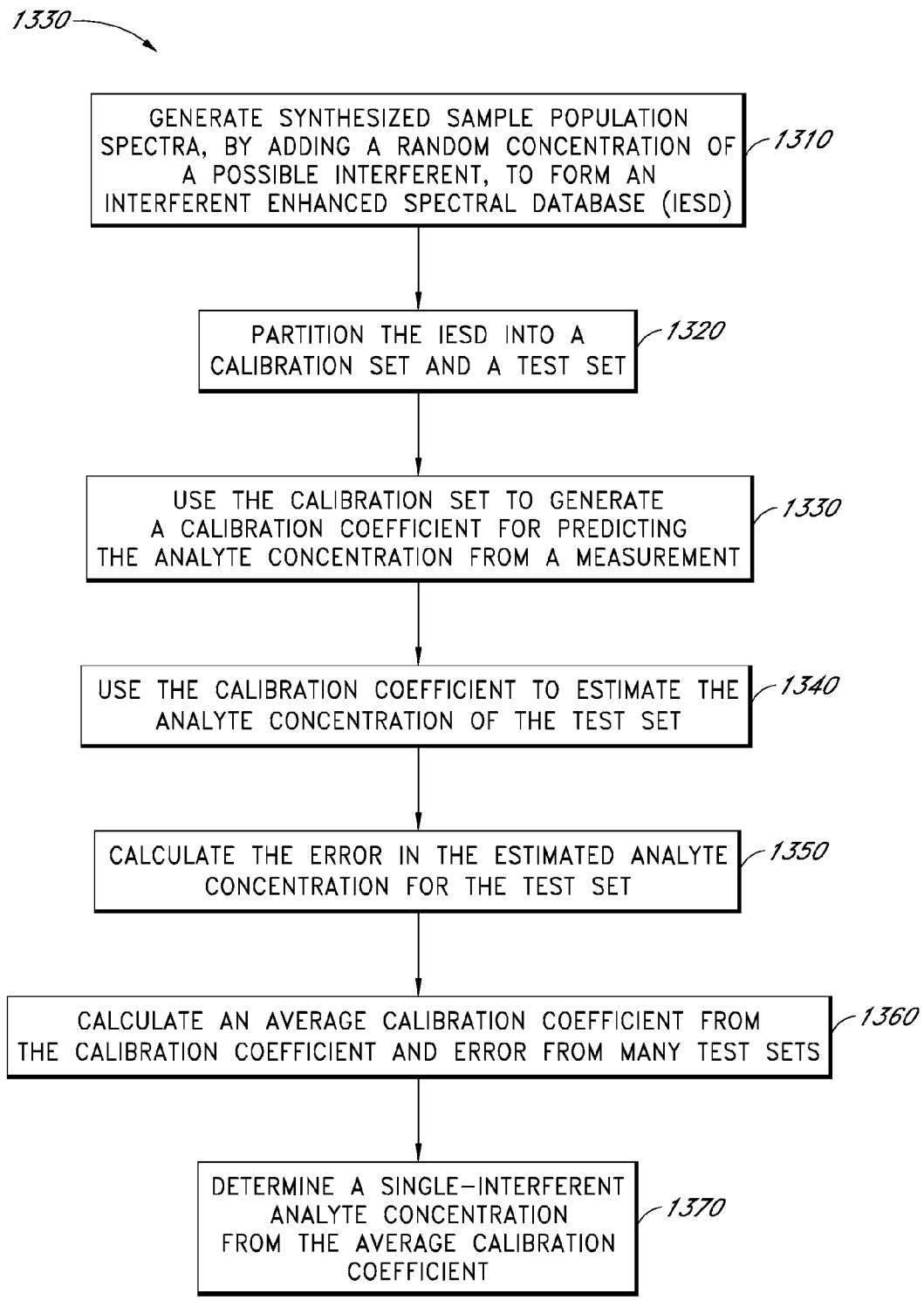
FIG. 13 is a flowchart that schematically illustrates an example embodiment of a method for estimating analyte concentration in the presence of the possible interferents.

Returning to FIG. 11, the method 1100 continues in block 1130 where analyte concentration is estimated in the presence of the possible interferents ξ determined in block 1250. FIG. 13 is a flowchart that schematically illustrates an example embodiment of the acts of block 1130. In block 1310, synthesized Sample Population measurements are generated to form an Interferent Enhanced Spectral Database (IESD). In block 1320, the spectra in the IESD are partitioned into a calibration set and a test. In block 1330, the calibration set is used to generate a calibration coefficient, and in block 1340, the calibration coefficient is used to estimate the analyte concentration of the test set. In block 1350, errors in the estimated analyte concentration of the test set are calculated, and in block 1360 an average calibration coefficient is calculated based on errors in the test set(s). In block 1370, the average calibration coefficient is applied to the measured spectra to determine an estimated single-interferent analyte concentration.

In certain embodiments, the blocks 1310-1360 are performed for each possible interferent ξ to provide a corresponding "single-interferent" average calibration coefficient for each particular interferent. In other embodiments, the blocks 1310-1360 are performed only for the single most probable interferent in the list identified in block 1250.

In one example embodiment for block 1310, synthesized Sample Population spectra are generated by adding a random concentration of one of the possible interferents ξ to each Sample Population spectrum. These spectra are referred to herein as an Interferent-Enhanced Spectral Database or IESD. In one method, the IESD is formed as follows. A plurality of Randomly-Scaled Single Interferent Spectra (RSIS) are formed by combinations of the interferent ξ having spectrum $IF_ξ$ multiplied by the maximum concentration $Tmax_m$, which is scaled by a random factor between zero and one. In certain embodiments, the scaling places the maximum concentration at the $95^{th}$ percentile of a log-normal distribution in order to generate a wide range of concentrations. In one embodiment, the log-normal distribution has a standard deviation equal to half of its mean value.

Individual RSIS are then combined independently and in random combinations to form a large family of Combination Interferent Spectra (CIS), with each spectrum within the CIS comprising a random combination of RSIS, selected from the full set of identified Library Interferents. An advantage of this method of selecting the CIS is that it produces adequate variability with respect to each interferent, independently across separate interferents.

The CIS and replicates of the Sample Population spectra are combined to form the IESD. Since the interferent spectra and the Sample Population spectra may have been obtained from measurements having different optical pathlengths, the CIS may be scaled to the same pathlength as the Sample Population spectra. The Sample Population Database is then replicated R times, where R depends on factors including the size of the Database and the number of interferents. The IESD includes R copies of each of the Sample Population spectra, where one copy is the original Sample Population Data, and the remaining R-1 copies each have one randomly chosen CIS spectra added. Accordingly, each of the IESD spectra has an associated analyte concentration from the Sample Population spectra used to form the particular IESD spectrum. In one embodiment, a 10-fold replication of the Sample Population Database is used for 130 Sample Population spectra obtained from 58 different individuals and 18 Library Interferents. A smaller replication factor may be used if there is greater spectral variety among the Library Interferent spectra, and a larger replication factor may be used if there is a greater number of Library Interferents.

After forming the IESD in block 1310, the blocks 1320-1350 may be executed to repeatedly combine different spectra of the IESD to statistically average out effects of the interferent. For example, in block 1320, the IESD may be partitioned into two subsets: a calibration set and a test set. Repeated partitioning of the IESD into different calibration and test sets improves the statistical significance of the calibration constant. In some embodiments, the calibration set includes a random selection of some of the IESD spectra, and the test set includes the remaining unselected IESD spectra. In one embodiment, the calibration set includes approximately two-thirds of the IESD spectra.

In block 1330, the calibration set is used to generate a calibration coefficient for estimating the analyte concentration from a sample measurement. In an implementation in which glucose concentration is to be determined from absorption measurements, a glucose absorption spectrum is obtained and indicated as $α_G$. The calibration coefficient is calculated in some embodiments as follows. Using the calibration set having calibration spectra $C=\{C_1, C_2, \ldots, C_n\}$ and corresponding glucose concentration values $G=\{g_1, g_2, \ldots, g_n\}$, glucose-free spectra $C'=\{C'_1, C'_2, \ldots, C'_n\}$ are calculated as: $C'_j=C_j-α_G g_j$. The calibration coefficient, K, is calculated from C' and $α_G$, according to the following 5 actions:

1) C' is decomposed into $C'=A_{C'}Δ_{C'}B_{C'}$, for example, by a singular value decomposition, where the A-factor is an orthonormal basis of column space, or span, of C';
2) $A_{C'}$ is truncated to avoid overfitting to a particular column rank r, based on the sizes of the diagonal entries of Δ (the singular values of C'). The selection of r involves a trade-off between the precision and stability of the calibration, with a larger r resulting in a more precise but less stable solution. In one embodiment, each spectrum C includes 25 wavelengths, and r ranges from 15 to 19;
3) The first r columns of $A_{C'}$ are taken as an orthonormal basis of span(C');
4) The projection from the background is found as the product $P_{C'}=A_{C'}A_{C'}^T$, e.g., the orthogonal projection onto the span of C'. The complementary, or nulling projection $P_{C'}^⊥=1-P_{C'}$, which forms the projection onto the complementary subspace $C'^⊥$, is calculated; and
5) The calibration coefficient κ is found by applying the nulling projection to the absorption spectrum of the analyte of interest: $K_{RAW}=P_{C'}^⊥α_G$ and normalizing the calibration coefficient $κ=κ_{RAW}/<κ_{RAW}, α_G>$, where the angle brackets <,> denote the standard inner (or dot) product of vectors. The normalized calibration coefficient produces a unit response for a unit $α_G$ spectral input for one particular calibration set.

In block 1340, the calibration coefficient is used to estimate the analyte concentration for the spectra in the test set. For example, each spectrum of the test set is multiplied by the calibration coefficient κ to calculate an estimated glucose concentration. Since each spectrum in the test set has a known glucose concentration, the error between the calculated and known glucose concentration may be calculated, in block 1350.

Blocks 1320-1350 may be repeated for a number of different random combinations of calibration sets. The number of combinations may be in a range from hundreds to thousands. In block 1360, an average calibration constant is calculated from the calibration coefficient and the error from the many calibration and test sets. For example, the average calibration coefficient may be computed as a weighted average of the individual calibration coefficients from the combinations. In one embodiment the weighting is in proportion to an inverse root-mean-square (rms), $\kappa_{ave} = \Sigma(\kappa^* \text{rms}^{-2})/\Sigma(\text{rms}^{-2})$ for all tests.

In summary, one embodiment of a method of computing a calibration constant based on an identified interferent ξ can be summarized as follows:

1. Generate synthesized Sample Population spectra by adding the RSIS to raw (interferent-free) Sample Population spectra, thus forming an Interferent Enhanced Spectral Database (IESD). Each spectrum of the IESD is synthesized from one spectrum of the Sample Population, and thus each spectrum of the IESD has at least one associated known analyte concentration
2. Separate the spectra of the IESD into a calibration set of spectra and a test set of spectra
3. Generate a calibration coefficient based on the calibration set spectra and their associated known analyte concentrations.
4. Use the calibration coefficient generated in (3) to calculate the error in the corresponding test set as follows (repeat for each spectrum in the test set):
    a. Multiply (the selected test set spectrum)×(average calibration constant generated in (3)) to generate an estimated glucose concentration
    b. Evaluate the difference between this estimated glucose concentration and the known glucose concentration associated with the selected test spectrum to generate an error associated with the selected test spectrum
5. Average the errors calculated in (4) to arrive at a weighted or average error for the current calibration set—test set pair
6. Repeat (2) through (5) a number n times, resulting in n calibration coefficients and n average errors
7. Compute a "grand average" error from the n average errors and an average calibration coefficient from the n calibration coefficient (preferably weighted averages wherein the largest average errors and calibration coefficient are discounted), to arrive at a calibration coefficient that has reduced or minimal sensitivity to the effect of the identified interferents The average calibration coefficient determined in block 1360 corresponds to a single interferent ξ from the list of possible interferents and is denoted herein as a single-interferent calibration coefficient $\kappa_{avg}(\xi)$. In block 1370 of FIG. 13, the single-interferent calibration coefficient is applied to the measured spectra $C_s$ to determine an estimated, single-interferent analyte concentration, $g(\xi) = \kappa_{avg}(\xi) \cdot C_s$ for the interferent ξ. The blocks 1310-1370 can be repeated for each of the interferents on the list of possible interferents, thereby providing an array of estimated, single-interferent analyte concentrations. As noted above, in some embodiments the blocks 1310-1360 are performed only once for the single most probable interferent on the list (e.g., the array of single-interferent analyte concentrations has a single member).

Returning to block 1140 of FIG. 11, the array of single-interferent concentrations, $g(\xi)$ are combined to determine an estimated analyte concentration, $g_{est}$, for the fluid sample. In certain embodiments, a weighting function $p(\xi)$ is determined for each of the interferents on the list of possible interferents. The weighting function may be normalized to unity, e.g., $\Sigma p(\xi) = 1$. For example, in some embodiments, the Raw Probability Score (RPS) (described above following Eq. (2)) is used in determining the weighting function. In one embodiment, the RPS's determined for the interferents on the list of possible interferents are rescaled to unit probability. The weighting function $p(\xi)$ equals the rescaled RPS and may be calculated according to $p(\xi) = RPS(\xi)/(\Sigma\ RPS(\xi))$, where the sum in the denominator is over all interferents ξ in the list. In other embodiments, different weighting functions can be used. For example, in one embodiment, the weighting function is the same constant value for each interferent.

In certain embodiments, the estimated analyte concentration, $g_{est}$, is determined by combining the single-interferent estimates, $g(\xi)$, and the weighting functions, $p(\xi)$, to generate a likelihood-weighted average analyte concentration. The likelihood-weighted average concentration may be computed according to $g_{est} = \Sigma\ g(\xi)\ p(\xi)$, where the sum is over all possible interferents. By testing the above described likelihood-weighted average method on simulated data, it has been found that the likelihood-weighted average analyte concentration advantageously has reduced errors compared to other methods (e.g., using only a single most probable interferent). In embodiments using a constant value for the weighting functions, the estimated analyte concentration is the arithmetic average of the single interferent concentrations.

In some embodiments, block 1370 of FIG. 13 is not performed and instead the estimated analyte concentration is determined in block 1140 of FIG. 11 by combining the single interferent calibration coefficients $\kappa_{avg}(\xi)$ (determined in block 1360) into a likelihood weighted average calibration coefficient according to $\kappa_{avg} = \Sigma \kappa(\xi) p(\xi)$. The estimated analyte concentration is determined from the average calibration coefficient and the spectral sample measurement according to $g_{est} = \kappa_{avg} \cdot C_s$. These embodiments determine the same estimated analyte concentration because of the linearity of the likelihood weighted average method.

The algorithm processor 416 may be configured, additionally or alternatively, to implement other methods for determining analyte concentration. For example, in certain embodiments, a parameter-free interferent rejection algorithm is implemented. In certain such embodiments, a sample measurement is obtained, substantially as described above in reference to block 1110 of FIG. 11. The algorithm processor 416, in block 1120, analyzes the obtained measurement to identify possible interferents. For example, the algorithm processor 416 may form a statistical sample population model and calculate statistical sample population parameters including mean spectra and covariance matrix (e.g., as described above with reference to block 1210 of FIG. 12). The processor 416 may then assemble a library of interferent data (e.g., as described above with reference to block 1220 of FIG. 12). The library may include interferent spectra, maximum plasma concentration, and a common random concentration distribution function for each interferent. In some embodiments, the processor 416 calculates a common variance (denoted by v) of the common random concentration distribution function.

The library may be divided into groups comprising some or all combinations of a number K of the library interferents. The number K may be an integer such as 1, 2, 3, 4, 5, 6, 7, 8, 15, 20, or more. A statistical test may then be performed to determine how well some or all of the groups of K library interferents fits the statistical population model. For example, the statistical test may provide a value for the Mahalanobis distance (of distance squared) for each group and/or an estimate of the concentration of some or all of the library interferents. In some embodiments, groups in which one or more estimated concentrations are negative are eliminated as being unphysical. In other embodiments, some or all groups having negative estimated concentrations may be retained, because they may indicate that the estimated concentration is lower than a standard or reference concentration (e.g., due to dilution of the sample measurement by saline or another fluid). A subset of the remaining groups may be selected, which provide the most likely interferents. For example, the subset may comprise the groups having a number N of the smallest values of the Mahalanobis distance (or distance squared). In various embodiments, the number N may be 1, 2, 5, 10, 20, 100, 200, or more. In certain embodiments, the subset is used to form a model group comprising some or all combinations of a number L of the groups in the subset. For example, the model group may comprise some or all combinations of pairs of subset groups (e.g., L=2). Because each group in the subset comprises K interferents and each model group comprises L subset groups, there are K*L interferents in each model group. For example, in an embodiment in which the each subset group comprises three interferents (K=3), and pairs of subset groups are combined (L=2), then each model group will have 3*2=6 interferents. Because interferents may be repeated when combinations of subset groups are formed, each model group will have between K+1 and K12 distinct interferents. For example, in the preceding example (K=3, L=2), there may be 4, 5, or 6 distinct interferents in any particular model group. The number of model groups may be determined from the well know formula for the number of combinations of the number N of subset groups taken L at a time: $C^N_L=N!/(L!*(N-L)!)$. For example, if N=100 subset groups are taken two at a time (e.g., pairs), then there will be 4950 model groups.

The algorithm processor 416 may then, in block 1130 of FIG. 11, generate a model for predicting the analyte concentration from the obtained sample measurement. For example, in some implementations, for some or all of the model groups, an average group interferent calibration coefficient is calculated, which accounts for the presence of the distinct interferents in any particular model group. The group interferent calibration coefficient may be calculated according to blocks 1310-1360 of FIG. 13 in some embodiments. In these embodiments, the group interferents are used, rather than a single interferent, in block 1310 to generate synthesized sample population spectra by adding random concentrations of each interferent present in the group to form an Interferent Enhanced Spectral Database (IESD). In block 1320, the IESD is partitioned into a calibration set and a test set. In block 1330, the calibration set is used to generate a calibration coefficient for estimating the analyte concentration in the presence of the interferents in the group. In block 1340, the calibration coefficient is used to estimate the analyte concentration of the test set, assuming the presence of that interferent group's interferents. In block 1350, the error is calculated in the estimated analyte concentration for the test set. Blocks 1320-1350 may be repeated one or more times to obtain group interferent calibration coefficients and errors for different combinations of calibration and test sets. In block 1360, an average group interferent calibration coefficient for each group is calculated from the results determined from blocks 1320-1350.

Returning to block 1140 shown in FIG. 11, the algorithm processor 416 may then use an average calibration coefficient to estimate analyte concentration from the obtained sample measurement. For example, in certain embodiments the average calibration coefficient is determined from an average of the group interferent calibration coefficients determined in block 1360. The average may be a straight average or a weighted average in various embodiments. The analyte concentration is determined by multiplying this average calibration coefficient by the measured spectra.

In other embodiments, the algorithm processor 416 uses different algorithms in block 1130 of FIG. 11 to determine an average calibration coefficient. For example, in some embodiments, every IESD is used as a calibration set, and there is no partition of the IESD into a calibration set and a test set and no error estimate is calculated. Accordingly, in some of these embodiments, the algorithm processor 416 may not perform blocks 1320, 1340, and 1350. The average calibration coefficient is determined, in block 1360 (or block 1370) from all the groups in the IESD.

In another embodiment, in block 1130, the average group calibration coefficient may be determined from the following actions.

1. From the group's $N_{IF}$ interferents, form an interferent spectra matrix, IF, having a mean $\overline{IF}$.
2. Calculate the covariance of the group's IF spectral set:

$$\Phi = \frac{1}{N_{IF}-1}[IF-\overline{IF}][IF-\overline{IF}]^T.$$

3. Calculate the group's covariance according to $K=K_0+\rho v\Phi$, where: $K_0$ is the covariance of the original sample population (from block 1120), $\rho$ is a weighting function that depends on the number of interferents in the group (e.g., $\rho=N_{IF}/(N_{IF}+1)$), and v is a variance of the (scalar) random concentration function.
4. Calculate all eigenvectors of K and their corresponding eigenvalues and sort them by decreasing magnitude. Typically, there is one eigenvector (eigenvalue) for each wavelength measured in the sample. The number of wavelengths is denoted by $N_W$.
5. Calculate a QR-decomposition of the matrix of sorted eigenvectors, yielding a matrix Q having orthonormal columns and rows.
6. For index n ranging from 2 to $N_W-1$, calculate the product $P^\parallel_n=Q(:,1:n)Q(:,1:n)^T$, where $Q(:,1:n)$ refers to a submatrix comprising the first n columns of the full matrix Q. Subtract $P^\parallel_n$ from the $N_w \times N_w$ identity matrix I, thereby yielding the orthogonal projection $P^\perp_n$ away from the space spanned by $Q(:,1:n)$. The $n^{th}$ calibration vector may be determined from $\kappa_n=P^\perp_n\alpha_G/\alpha_G^T P^\perp_n\alpha_G$, where $\alpha_G$ represents the analyte absorption spectrum. The $n^{th}$ error variance $V_n$ may be determined as the projection of the full covariance K onto the subspace spanned by $\kappa_n$ as follows: $V_n=\kappa_n^T K \kappa_n$
7. The average group calibration coefficient $\kappa$ may be selected to be the $m^{th}$ calibration vector $\kappa_m$ for the value of m at which the minimum value for the error variance $V_m$ is attained.

A possible advantage of the foregoing algorithms is more rapid execution time by the algorithm processor 416, because the calibration coefficient is computed directly, without synthesizing spectra or breaking the data into calibration and test sets. In other embodiments, a skilled artisan will recognize that regression, partial least squares, and/or principal component resolution techniques may be used to determine the average group calibration coefficient.

User Interface

The system 400 may include a display controller 414, for example, as depicted in FIG. 4. The display controller 414 may comprise an input device including, for example, a keypad or a keyboard, a mouse, a touchscreen display, and/or any other suitable device for inputting commands and/or information. The display controller 414 may also include an output device including, for example, an LCD monitor, a CRT monitor, a touchscreen display, a printer, and/or any other suitable device for outputting text, graphics, images, videos, etc. In some embodiments, a touchscreen display is advantageously used for both input and output.

The display controller 414 may include a user interface 1400 by which users can conveniently and efficiently interact with the system 400. The user interface 1400 may be displayed on the output device of the system 400 (e.g., the touchscreen display).

FIGS. 14A and 14B schematically illustrate the visual appearance of embodiments of the user interface 1400. The user interface 1400 may show patient identification information 1402, which may include patient name and/or a patient ID number. The user interface 1400 also may include the current date and time 1404. An operating graphic 1406 shows the operating status of the system 400. For example, as shown in FIGS. 14A and 14B, the operating status is "Running," which indicates that the system 400 is fluidly connected to the patient ("Jill Doe") and performing normal system functions such as infusing fluid and/or drawing blood. The user interface 1400 can include one or more analyte concentration graphics 1408, 1412, which may show the name of the analyte and its last measured concentration. For example, the graphic 1408 in FIG. 14A shows "Glucose" concentration of 150 mg/dl, while the graphic 1412 shows "Lactate" concentration of 0.5 mmol/L. The particular analytes displayed and their measurement units (e.g., mg/dl, mmol/L, or other suitable unit) may be selected by the user. The size of the graphics 1408, 1412 may be selected to be easily readable out to a distance such as, e.g., 30 feet. The user interface 1400 may also include a next-reading graphic 1410 that indicates the time until the next analyte measurement is to be taken. In FIG. 14A, the time until next reading is 3 minutes, whereas in FIG. 14B, the time is 6 minutes, 13 seconds.

The user interface 1400 may include an analyte concentration status graphic 1414 that indicates status of the patient's current analyte concentration compared with a reference standard. For example, the analyte may be glucose, and the reference standard may be a hospital ICU's tight glycemic control (TGC). In FIG. 14A, the status graphic 1414 displays "High Glucose," because the glucose concentration (150 mg/dl) exceeds the maximum value of the reference standard. In FIG. 14B, the status graphic 1414 displays "Low Glucose," because the current glucose concentration (79 mg/dl) is below the minimum reference standard. If the analyte concentration is within bounds of the reference standard, the status graphic 1414 may indicate normal (e.g., "Normal Glucose"), or it may not be displayed at all. The status graphic 1414 may have a background color (e.g., red) when the analyte concentration exceeds the acceptable bounds of the reference standard.

The user interface 1400 may include one or more trend indicators 1416 that provide a graphic indicating the time history of the concentration of an analyte of interest. In FIGS. 14A and 14B, the trend indicator 1416 comprises a graph of the glucose concentration (in mg/dl) versus elapsed time (in hours) since the measurements started. The graph includes a trend line 1418 indicating the time-dependent glucose concentration. In other embodiments, the trend line 1418 may include measurement error bars and may be displayed as a series of individual data points. In FIG. 14B, the glucose trend indicator 1416 is shown as well as a trend indicator 1430 and trend line 1432 for the lactate concentration. In some embodiments, a user may select whether none, one, or both trend indicators 1416, 1418 are displayed. In certain embodiments, one or both of the trend indicators 1416, 1418 may appear only when the corresponding analyte is in a range of interest such as, for example, above or below the bounds of a reference standard.

The user interface 1400 may include one or more buttons 1420-1426 that can be actuated by a user to provide additional functionality or to bring up suitable context-sensitive menus and/or screens. For example, in the embodiments shown in FIGS. 14A and 14B, four buttons 1420-1426 are shown, although fewer or more buttons are used in other embodiments. The button 1420 ("End Monitoring") may be pressed when one or both of the disposable cassettes 610, 612 (see FIG. 6) are to be removed. In many embodiments, because the cassettes 610, 612 are not reusable, a confirmation window appears when the button 1420 is pressed. If the user is certain that monitoring should stop, the user can confirm this by actuating an affirmative button in the confirmation window. If the button 1420 were pushed by mistake, the user can select a negative button in the confirmation window. If "End Monitoring" is confirmed, the system 400 performs appropriate actions to cease fluid infusion and blood draw and to permit ejection of one (or both) cassettes 610, 612.

The button 1422 ("Pause") may be actuated by the user if patient monitoring is to be interrupted but is not intended to end. For example, the "Pause" button 1422 may be actuated if the patient is to be temporarily disconnected from the system 400 (e.g., by disconnecting the tubes 306). After the patient is reconnected, the button 1422 may be pressed again to resume monitoring. In some embodiments, after the "Pause" button 1422 has been pressed, the button 1422 displays "Resume."

The button 1424 ("Delay 5 Minutes") causes the system 400 to delay the next measurement by a delay time period (e.g., 5 minutes in the depicted embodiments). Actuating the delay button 1424 may be advantageous if taking a reading would be temporarily inconvenient, for example, because a health care professional is attending to other needs of the patient. The delay button 1424 may be pressed repeatedly to provide longer delays. In some embodiments, pressing the delay button 1424 is ineffective if the accumulated delay exceeds a maximum threshold. The next-reading graphic 1410 automatically increases the displayed time until the next reading for every actuation of the delay button 1424 (up to the maximum delay).

The button 1426 ("Dose History") may be actuated to bring up a dosing history window that displays patient dosing history for an analyte or medicament of interest. For example, in some embodiments, the dosing history window displays insulin dosing history of the patient and/or appropriate hospital dosing protocols. A nurse attending the patient can actuate the dosing history button 1426 to determine the time when the patient last received an insulin dose, the last dosage amount, and/or the time and amount of the next dosage. The system 400 may receive the patient dosing history via wired or wireless communications from a hospital information system.

In other embodiments, the user interface 1400 may include additional and/or different buttons, menus, screens, graphics, etc. that are used to implement additional and/or different functionalities.

Related Components

Figure 15:
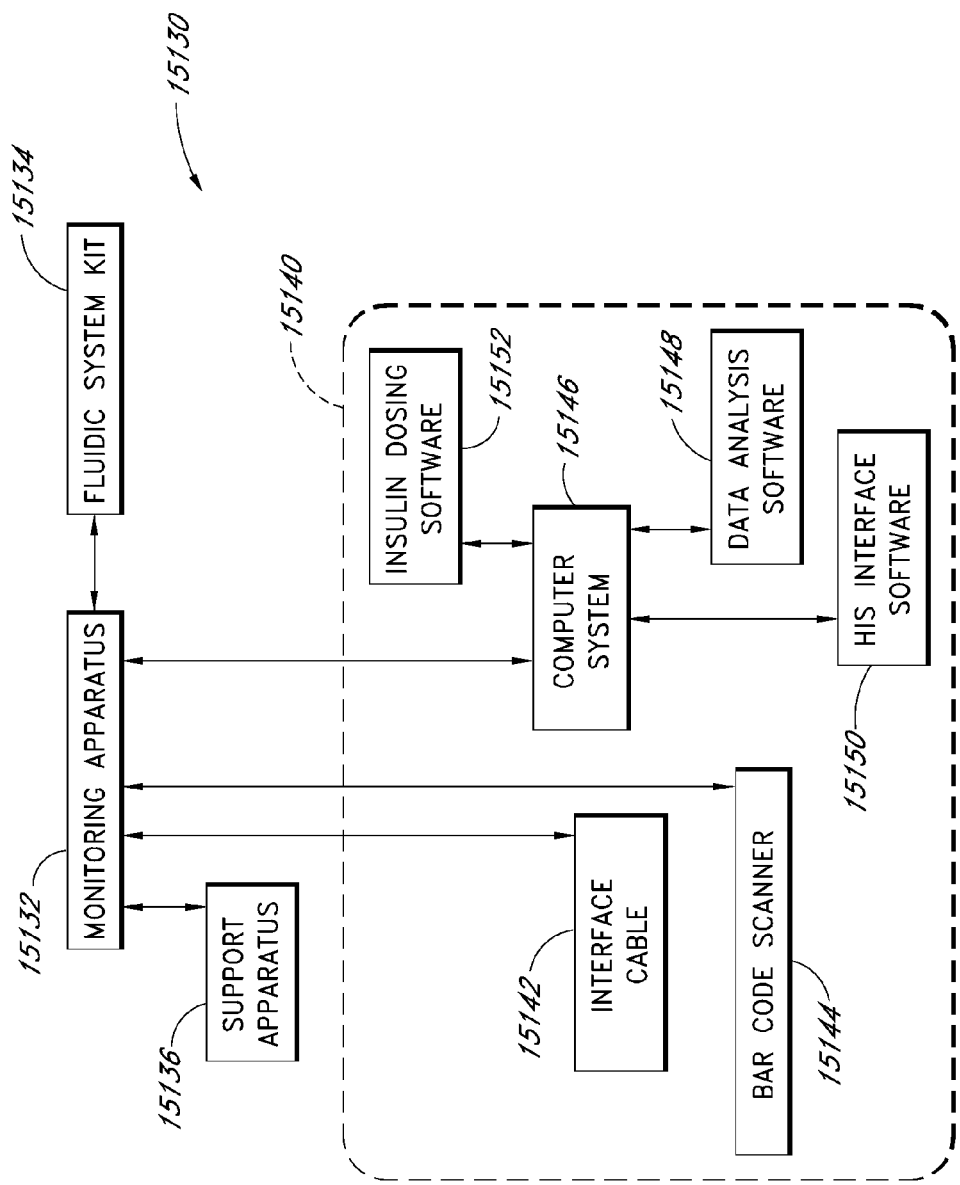
FIG. 15 schematically depicts various components and/or aspects of a patient monitoring system and the relationships among the components and/or aspects.

FIG. 15 schematically depicts various components and/or aspects of a patient monitoring system 15130 and how those components and/or aspects relate to each other. Some of the depicted components can be included in a kit containing a plurality of components. Some of the depicted components, including, for example, the components represented within the dashed rounded rectangle 15140 of FIG. 15, are optional and/or can be sold separately from other components.

The patient monitoring system 15130 shown in FIG. 15 includes a monitoring device 15132. The monitoring device 15132 can provide monitoring of physiological parameters of a patient. In some embodiments, the monitoring device 15132 measures glucose and/or lactate concentrations in the patient's blood. In some embodiments, the measurement of such physiological parameters is substantially continuous. The monitoring device 15132 may also measure other physiological parameters of the patient. In some embodiments, the monitoring device 15132 is used in an intensive care unit (ICU) environment. In some embodiments, one monitoring device 15132 is allocated to each patient room in an ICU.

The patient monitoring system 15130 can include an optional interface cable 15142. In some embodiments, the interface cable 15142 connects the monitoring device 15132 to a patient monitor (not shown). The interface cable 15142 can be used to transfer data from the monitoring device 15132 to the patient monitor for display. In some embodiments, the patient monitor is a bedside cardiac monitor having a display that is located in the patient room. In some embodiments, the interface cable 15142 transfers data from the monitoring device 15132 to a central station monitor and/or to a hospital information system (HIS). The ability to transfer data to a central station monitor and/or to a HIS may depend on the capabilities of the patient monitor system.

In the embodiment shown in FIG. 15, an optional bar code scanner 15144 is connected to the monitoring device 15132. In some embodiments, the bar code scanner 15144 is used to enter patient identification codes, nurse identification codes, and/or other identifiers into the monitoring device 15132. In some embodiments, the bar code scanner 15144 contains no moving parts. The bar code scanner 15144 can be operated by manually sweeping the scanner 15144 across a printed bar code or by any other suitable means. In some embodiments, the bar code scanner 15144 includes an elongated housing in the shape of a wand.

The patient monitoring system 15130 includes a fluidic system kit 15134 connected to the monitoring device 15132. In some embodiments, the fluidic system kit 15134 includes fluidic tubes that connect a fluid source to an analytic subsystem. For example, the fluidic tubes can facilitate fluid communication between a blood source or a saline source and an assembly including a flow cell and/or a centrifuge. In some embodiments, the fluidic system kit 15134 includes many of the components that enable operation of the monitoring device 15132. In some embodiments, the fluidic system kit 15134 can be used with anti-clotting agents (such as heparin), saline, a saline infusion set, a patient catheter, a port sharing IV infusion pump, and/or an infusion set for an IV infusion pump, any or all of which may be made by a variety of manufacturers. In some embodiments, the fluidic system kit 15134 includes a monolithic housing that is sterile and disposable. In some embodiments, at least a portion of the fluidic system kit 15134 is designed for single patient use. For example, the fluidic system kit 15134 can be constructed such that it can be economically discarded and replaced with a new fluidic system kit 15134 for every new patient to which the patient monitoring system 15130 is connected. In addition, at least a portion of the fluidic system kit 15134 can be designed to be discarded after a certain period of use, such as a day, several days, several hours, three days, a combination of hours and days such as, for example, three days and two hours, or some other period of time. Limiting the period of use of the fluidic system kit 15134 may decrease the risk of malfunction, infection, or other conditions that can result from use of a medical apparatus for an extended period of time.

In some embodiments, the fluidic system kit 15134 includes a connector with a luer fitting for connection to a saline source. The connector may be, for example, a three-inch pigtail connector. In some embodiments, the fluidic system kit 15134 can be used with a variety of spikes and/or IV sets used to connect to a saline bag. In some embodiments, the fluidic system kit 15134 also includes a three-inch pigtail connector with a luer fitting for connection to one or more IV pumps. In some embodiments, the fluidic system kit 15134 can be used with one or more IV sets made by a variety of manufacturers, including IV sets obtained by a user of the fluidic system kit 15134 for use with an infusion pump. In some embodiments, the fluidic system kit 15134 includes a tube with a low dead volume luer connector for attachment to a patient vascular access point. For example, the tube can be approximately seven feet in length and can be configured to connect to a proximal port of a cardiovascular catheter. In some embodiments, the fluidic system kit 15134 can be used with a variety of cardiovascular catheters, which can be supplied, for example, by a user of the fluidic system kit 15134.

As shown in FIG. 15, the monitoring device 15132 is connected to a support apparatus 15136, such as an IV pole. The support apparatus 15136 can be customized for use with the monitoring device 15132. A vendor of the monitoring device 15132 may choose to bundle the monitoring device 15132 with a custom support apparatus 15136. In one embodiment, the support apparatus 15136 includes a mounting platform for the monitoring device 15132. The mounting platform can include mounts that are adapted to engage threaded inserts in the monitoring device 15132. The support apparatus 15136 can also include one or more cylindrical sections having a diameter of a standard IV pole, for example, so that other medical devices, such as IV pumps, can be mounted to the support apparatus. The support apparatus 15136 can also include a clamp adapted to secure the apparatus to a hospital bed, an ICU bed, or another variety of patient conveyance device.

In the embodiment shown in FIG. 15, the monitoring device 15132 is electrically connected to an optional computer system 15146. The computer system 15146 can be used to communicate with one or more monitoring devices. In an ICU environment, the computer system 15146 can be connected to at least some of the monitoring devices in the ICU. The computer system 15146 can be used to control configurations and settings for multiple monitoring devices (for example, the system can be used to keep configurations and settings of a group of monitoring devices common). The computer system 15146 can also run optional software, such as data analysis software 15148, HIS interface software 15150, and insulin dosing software 15152.

In some embodiments, the computer system 15146 runs optional data analysis software 15148 that organizes and presents information obtained from one or more monitoring devices. In some embodiments, the data analysis software

15148 collects and analyzes data from the monitoring devices in an ICU. The data analysis software 15148 can also present charts, graphs, and statistics to a user of the computer system 15146.

In some embodiments, the computer system 15146 runs optional hospital information system (HIS) interface software 15150 that provides an interface point between one or more monitoring devices and an HIS. The HIS interface software 15150 may also be capable of communicating data between one or more monitoring devices and a laboratory information system (LIS).

In some embodiments, the computer system 15146 runs optional insulin dosing software 15152 that provides a platform for implementation of an insulin dosing regimen. In some embodiments, the hospital tight glycemic control protocol is included in the software. The protocol allows computation of proper insulin doses for a patient connected to a monitoring device 15146. The insulin dosing software 15152 can communicate with the monitoring device 15146 to ensure that proper insulin doses are calculated.

Inhibiting Blood Clot Formation

The coagulation of blood may affect the operation of blood systems (e.g., extracorporeal blood systems). In general, coagulation proceeds according to a series of complex chemical reactions within the blood. In extracorporeal systems, coagulation may begin upon the contact of blood with most types of surfaces, and coagulated blood may collect on surfaces or within crevices. Blood coagulation may also be associated with changes in surface type or flow conditions. Thus, for example, blood flowing through passageways may build up on the passageway walls or may form clots that restrict or block the flow of blood, hindering the operation of the system. This section is directed to several devices and methods for inhibiting blood clot formation in system 100 (FIG. 3).

Ultrasonic Inhibition of Blood Clots

It has been found by the inventors that the application of vibrations to an extracorporeal system dissolves and disrupts blood clots within the system, thereby preventing clogging of the fluid passages. The vibrations are preferably at frequencies above the range of human hearing, such as greater than 15 kHz, and these vibrations are referred to herein and without limitation as ultrasonic vibrations or waves, or as "ultrasound."

Figure 16:
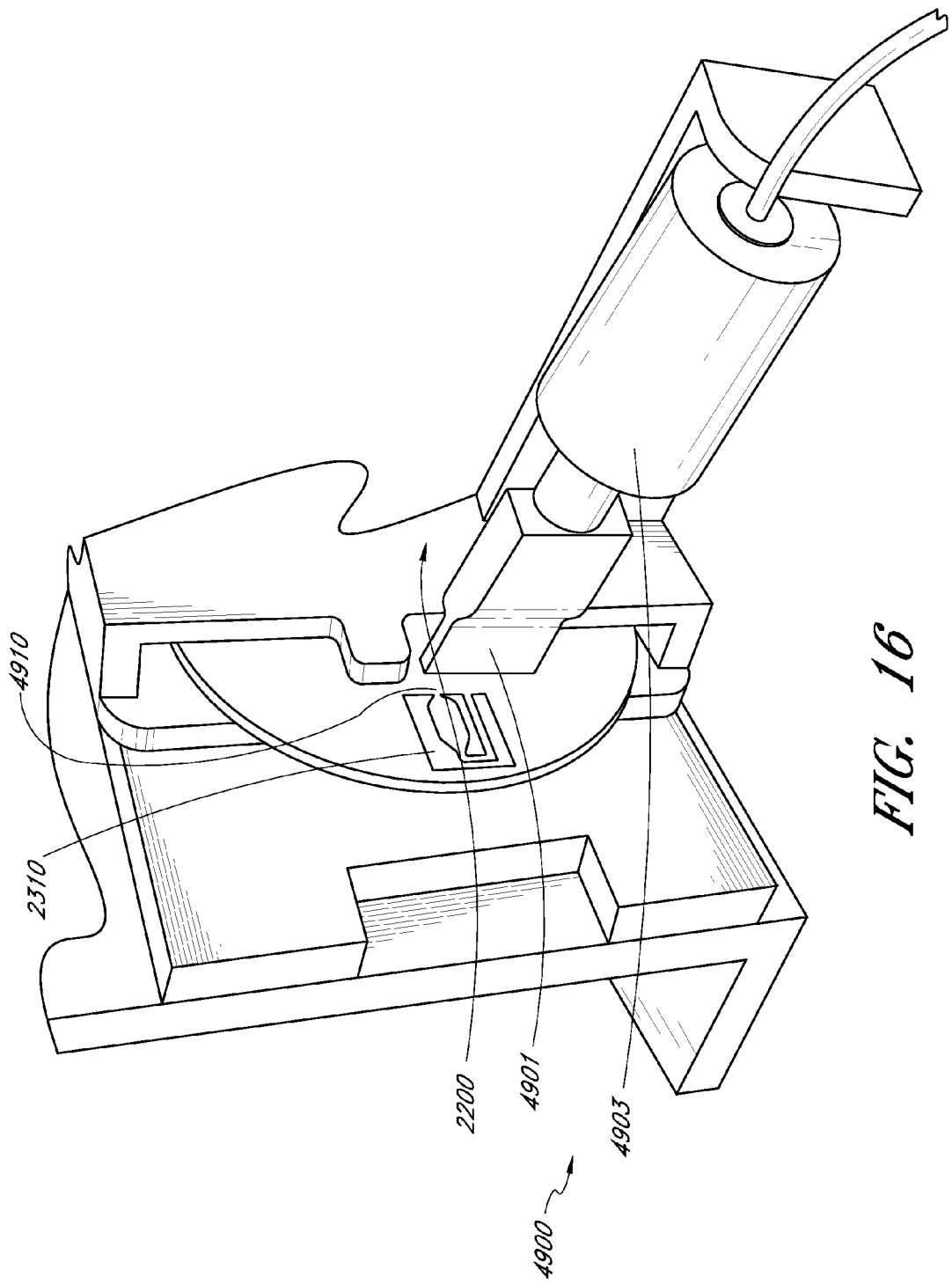
FIG. 16 is perspective view of an embodiment anti-clotting device showing an ultrasonic generator adjacent to a centrifuge.

An illustrative embodiment will now be presented with reference to FIG. 16. The discussion in terms of the following embodiment is not meant to limit the scope of either the apparatus or methods of the present disclosure. Specifically, FIG. 16 is a perspective view of an embodiment of an anti-clotting device 4900 including an ultrasonic horn 4901 and an ultrasonic generator 4903. The ultrasonic horn 4901 is positioned adjacent to flow passageways 4910, which are in turn adjacent to a sample element 2310. The ultrasonic generator 4903 is preferably connected to a power supply and electronics (not shown). In some embodiments, the ultrasonic horn 4901 is movable and may be placed in contact with a blood-containing portion of an extracorporeal system, for example passageways 4901, with vibrations directed towards a location where clots are known or expected to form.

In some embodiments, the frequency transmitted through the ultrasonic horn 4901 is in a range of approximately 15 to 60 kHz, and the horn 4901 can transmit from approximately 2 to approximately 200 Watts of ultrasonic power. In one preferred embodiment, a model VC24 ultrasonic system obtained from Sonics & Materials, Inc (Newtown, Conn.) can be operated at a frequency of 40 kHz and 25 Watts of power.

As an example of the use of the apparatus of FIG. 16, repeated filling of the sample element 2310 with whole blood in the absence of ultrasound resulted in visible clogging. Device 4900 was then tested by repeatedly filling the sample element 2310 with whole blood, bringing the horn 4901 into contact with the passageway 4910, and activating generator 4903 to deliver a 10 second pulse of 40 kHz, 25 Watt ultrasound. This 10-second pulse was delivered between each filling of sample element 2301. The filling and providing of ultrasound was repeated every 30 minutes for 69 hours, after which there was very little evidence of clogging, either visually or by measuring the inhibition of blood flowing through the passageway.

Inhibition of Blood Clots with Cleaning Solution

Figure 17:
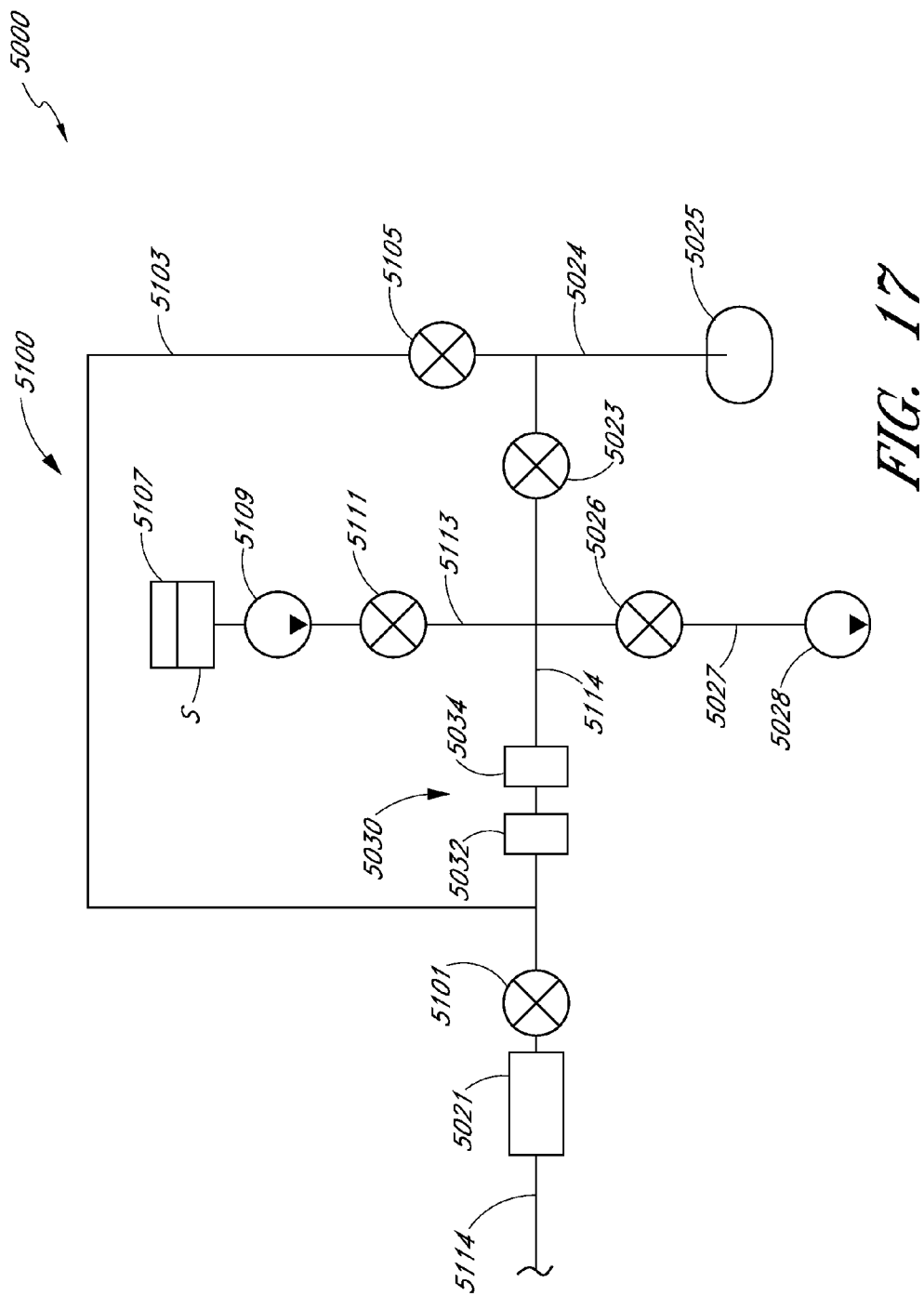
FIG. 17 is a schematic showing details of an alternative embodiment of a sampling apparatus.

Some embodiments include an additional or alternative approach. For example, clotting can be inhibited or prevented by providing a cleaning solution to the flow passageways. In one such embodiment, a cleaning solution S is provided at intervals to some or all of the passageways 306 (FIG. 3) connecting the components of the system 100. One illustration of this concept is described with reference to FIG. 17. The discussion in terms of the following embodiment is not meant to limit the scope of either the apparatus or methods of the present disclosure. Specifically, FIG. 17 is a schematic showing details of a sampling system 5000 which may be generally similar to the embodiments of sampling system 100 as illustrated in FIG. 3. The sampling system 5000 may also have additional and/or modified features.

The sampling system 5000 includes an embodiment of an anti-clotting device 5100 to provide cleaning solution S contained in a cleaning solution container 5107 and delivered through a passageway 5113 into a passageway 5114 and a sample analysis device 5030. In particular, the device 5100 includes a pump 5109 and a valve 5111 on the passageway 5113, a valve 5101 on the passageway 5114, and a bypass 5103 having a valve 5105. The valves and pumps of the device 5100 are connected to and controlled by a controller through electrical control lines that are not shown in FIG. 17.

The device 5100 may be used to flush cleaning solution S through the passageway 5114 and the sample analysis device 5030 as follows. After a fluid is sampled and analyzed by the sampling system 5000, the valves 5101, 5023, and 5026 are closed, the valves 5111 and 5105 are opened, and the pump 5109 is activated. At that time, cleaning solution S is pumped from the container 5107 into the passageways 5113, 5114, and 5024, and through the device 5030. This pumping action is a backflow—that is, it is in the reverse direction of the normal flow of the system 5000. After a sufficient amount of cleaning solution has been provided to the system 5000, the valves 5101, 5023, and 5026 are opened, the valves 5111 and 5105 are closed, and pump 5109 is stopped. Residual blood, saline, or other fluids are then pumped, using another pump (not shown), into a waste receptacle 5025. Fluid sampling and analysis may then be carried out again and the process can repeat.

In some embodiments, the cleaning solution S is effective in removing blood, blood components, and/or clotted blood from the surfaces of the passageways, sample elements, or other blood contacting surfaces. It is preferred that solution S is thermally stable at room temperatures. Appropriate cleaning solutions can be selected from those typically used for cleaning hospital and laboratory instruments, and these solutions may include nonspecific protease enzymes for digesting blood. One appropriate type of cleaning solution S is a mixture of approximately 1% TERGAZYME™ (manufactured by Alconox, Inc., White Planes, N.Y.) in saline.

Anticoagulant Inhibition of Blood Clots

Figure 18:
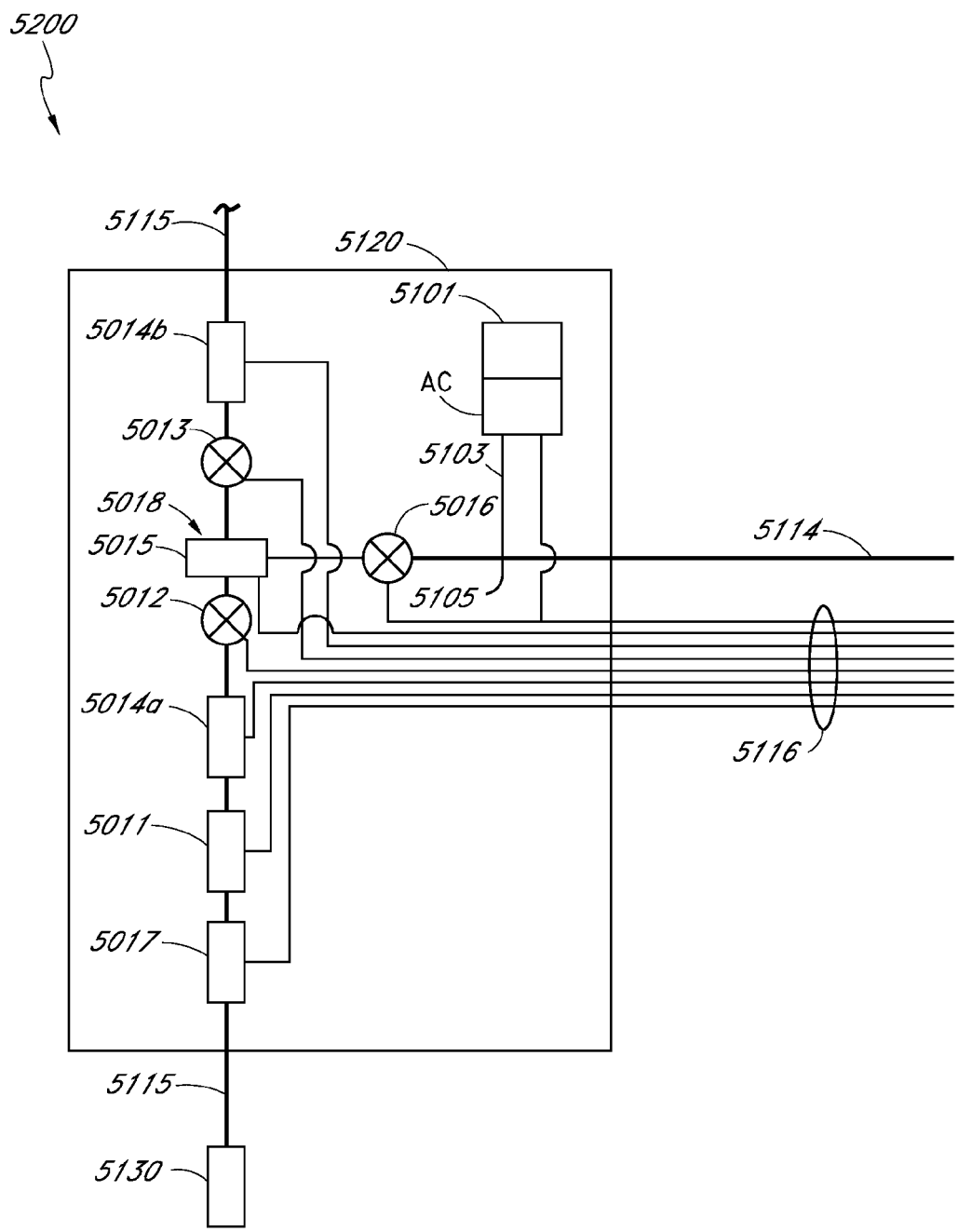
FIG. 18 is a schematic showing details of another alternative embodiment of a sampling apparatus.

Some embodiments prevent clotting by providing an anticoagulant solution to bodily fluids in passageways 306. One illustration of this embodiment is now presented with reference to FIG. 18, which is not meant to limit the scope of the present disclosure. FIG. 18 is a schematic showing details of a sampling system 5200 which may be generally similar to the embodiments of sampling system 100 as illustrated in FIG. 3. The sampling system 5200 may also have additional and/or modified features. A sampling assembly 5120 of the sampling system 5200 may be generally similar to the embodiment of the fluid system 510 as illustrated in FIG. 5, except as further detailed below. The sampling assembly 5120 may also have additional and/or modified features.

The sampling system 5200 includes an embodiment of an anticoagulant supply 5101 to provide a solution—referred to herein and without limitation as an "anticoagulant solution" AC—to bodily fluids within passageway 5114. In the embodiment of FIG. 18, the anticoagulant solution AC has blood anticoagulant properties and is delivered through a passageway 5103 into a passageway 5114 at a junction 5105. It is preferred that the anticoagulant supply 5101 includes an amount of anticoagulant solution AC to operate for some period of time, such as up to 1 hour, 6 hours, 1 day, 2 days, 3 days, more than 3 days, or another period.

The sampling system 5200 also includes a line 5116 to a controller (not shown). The anticoagulant supply 5101, under the control of the controller, delivers the solution through the passageway 5103, where it mixes with fluid in the passageway 5114 at the junction 5105. In some embodiments, the anticoagulant supply 5101 includes a mechanism to deliver a controlled and/or repeatable quantity of anticoagulant solution AC. Thus, for example, the anticoagulant supply 5101 includes a positive displacement pump, including but not limited to an ink jet-type or automated syringe pump. In another embodiment, the anticoagulant supply 5101 includes a valve and anticoagulant solution AC is supplied by a low pressure in the passageway 5114.

As described subsequently, the term "anticoagulant solution" refers to a solution that is added to a material sample of bodily fluid that has anticoagulant properties, and is not meant to be limiting as to the composition of anticoagulant solution AC. In general, anticoagulant solution AC includes one or more anticoagulants and may optionally include a solvent, such as water, and other components that may be necessary to stabilize the anticoagulants. Some embodiments of an anticoagulant solution AC include components that aid in quantifying the amount of the anticoagulant solution AC added to passageway 5114 and that may have little or no anticoagulant properties or be related to the functioning or use of the anticoagulants, as discussed subsequently.

Preferably, the solution provided into the passageway 5103 contains a sufficient amount of one or more anticoagulants to inhibit or prevent the coagulation of blood in the passageway 5114. Anticoagulants that may be used in various embodiments include, but are not limited to sodium heparin, ethylenediaminetetraacetic acids, including but not limited to, dipotassium dthylenediamine tetraacetic acid ($K_2$EDTA) and tripotassium ethylenediamine tetraacetic acid ($K_3$EDTA), potassium oxalate, and sodium citrate in an aqueous solution. The concentration of these anticoagulants sufficient for inhibiting coagulation is well known in the field, and is summarized in the following table. It is preferred that the flow of anticoagulant in the passageway 5103 and the flow of blood in the passageway 5114 be selected so that the anticoagulant concentration in the blood is sufficient to inhibit coagulation. The solution provided into the passageway 5103 may contain one or more of the anticoagulants listed in Table 5 and/or other compounds.

TABLE 5

Partial List of Suitable Anticoagulants.

| Anticoagulant | Approximate Concentration in mg/dL |
|---|---|
| Sodium Heparin | 10.2 mg/dL (150 Units/10 mL) |
| K2EDTA | 175 mg/dL |
| K3EDTA | 175 mg/dL |
| Potassium Oxalate/sodium fluoride (for glycolic inhibition) | 200 mg/dL/250 mg/dL |
| Sodium Citrate/Citric acid (buffered solution) | 355 mg/dL/46.7 mg/dL |

The operation of the sampling system 5200 is generally similar to the method of operating described previously with reference to FIG. 5. In some embodiments, one or more steps result in the injection of an anticoagulant AC. The junction 5105 is located near the valve 5016, as shown in FIG. 18. A controller provides instructions to the sampling system 5120 to supply anticoagulant AC into all or some of sample S just after passing the valve 5016. For example, the anticoagulant AC can be supplied after air is injected into the sample. The sample measured by the sampling unit is a mixture of the sample S and the anticoagulant solution AC, referred to herein as a mixture S/AC.

Obtaining measurements on the mixture S/AC may require a change of the method used to analyze the measurements over making measurements on pure sample S alone. The following is a list of several methods, which is not meant to be limiting, of analyzing the mixture S/AC to obtain measurements of one or more analytes in the mixture S/AC.

In some embodiments, the components of anticoagulant solution AC are of a sufficiently small concentration or volume when mixed with sample S that they do not have a signature detectable by the sampling unit. In this case, some of the methods described herein can still be used to measure analytes in the mixture S/AC.

In some embodiments, the components of anticoagulant solution AC are detectable by the sampling unit at levels that affect the measurement of analytes. In this scenario, the anticoagulant solution components are exogenous interferents that need to be accounted for. Thus, for example, components of anticoagulant solution AC that affect the measurement of analytes may be included as Library Interferents. The method described herein can then be used to measure analytes in the mixture S/AC.

The addition of a volume of anticoagulant solution AC to solution S changes the concentration of analyte being measured. Thus, for example a concentration of an analyte in solution S may be diluted to a lower concentration in the mixture S/AC. In some embodiments, the dilution is not accounted for—that is the system measures and reports the concentration of analyte in mixture S/AC. This is the preferable method for conditions where the dilution is small enough so that the resulting dilution error is below a threshold level. In another embodiment, the measured analyte concentration in mixture S/AC is corrected to provide an estimate of the analyte concentration in the undiluted mixture S.

There are several alternative embodiments for correcting for dilution due to the addition of anticoagulant solution anticoagulant solution AC based on determining the amount of dilution that occurs from adding a volume of anticoagulant solution. Some embodiments include using an anticoagulation solution AC that has a component that is quantifiable in sampling system 100. In general, a mixture of compounds used for anticoagulation purposes, including, possibly, a solvent and a stabilizer (an "anticoagulation mixture"), are either quantifiable or are not quantifiable in sampling system 100. It is preferable that the quantifiable compound (referred to herein, without limitation, as an "anticoagulation analyte"), be it an anticoagulant or added quantifiable compound, is neither an endogenous interferent nor an endogenous analyte.

For infrared spectroscopic analyte detection systems, including but not limited to the analyte detection system 910, examples of anticoagulant solutions that are quantifiable include, but are not limited to, mixtures of one or more of heparin, sodium heparin, $K_2$EDTA, $K_3$EDTA, potassium oxalate, and sodium citrate.

Anticoagulant analytes useful in infrared spectroscopic analyte detection systems, including but not limited to analyte detection system 910, can be compounds that are inert, water-soluble, stable and that have identifiable infrared spectrum. In some embodiments, added anticoagulation analytes have a small number of infrared absorbance peaks that preferably do not overlap those of the analytes or interferents. In some embodiments, the added anticoagulation analyte has a distinctive spectrum in a range of from 4 to 6 µm and/or from 7.5 to 8.5 µm.

In some embodiments, sodium bicarbonate is added as an anticoagulation analyte. Sodium bicarbonate is relatively inert towards blood analytes of interest, and has a simple absorption spectrum with a major peak around 8.5 micrometers. In some embodiments, sodium borate salts are another added anticoagulation analyte. Other anticoagulation analytes include, but are not limited to, small, symmetric compounds of preferably two elements, including but not limited to oxides of B, C, N, Al, Si, P, S, and Se.

The following discussion is directed to methods for correcting for dilution due to the addition of an anticoagulant that contains an anticoagulation analyte. For discussion purposes, assume that the mixture S/AC is an ideal mixture. As one example, assume that an analyte having a concentration $C0$ in volume $V0$ of sample S is diluted with $\delta V$ of anticoagulant solution AC. Equating the amount of analyte in the undiluted sample S and diluted mixture S/AC gives:

$$C0 = C0'(1+\delta V/V0). \qquad \text{Equation (1)}$$

In a first embodiment, sampling system 5200 supplies either reproducible volumes of solution AC ($\delta V$) and solution S ($V0$) or a reproducible ratio of volumes ($\delta V/V0$). The ratio $\delta V/V0$ is then determined directly or by calibration using known sample concentrations, and Equation (1) is used to correct for dilution.

In a second embodiment, sampling system 5200 supplies accurately measured volumes of either anticoagulant solution AC ($\delta V$) or solution S ($V$) and a measurement is made of the amount of anticoagulation analyte in sampling system 100. Assume, for example, that anticoagulation analyte has a known concentration $C1$ in anticoagulant solution AC. Upon dilution of a volume $\delta V$ of anticoagulant solution AC in mixture S/AC, the concentration of the anticoagulation analyte in mixture S/AC will be diluted to a value of $C1'$. Conservation of mass of the measurable anticoagulant analyte gives:

$$C1' = C1\delta V/(V0+\delta V), \qquad \text{Equation (2)}$$

and the volume ratio $\delta V/V0$ in mixture can be calculated from Equation (2) as:

$$\delta V/V0 = C1'/(C1-C1'). \qquad \text{Equation (3)}$$

Equations (1) and (3) then give:

$$C0 = C0'C1/(C1-C1'). \qquad \text{Equation (4)}$$

Given the known anticoagulation analyte concentration in the anticoagulation solution ($C1$) and the measured anticoagulation analyte concentration and analyte concentration in the mixture S/AC ($C1'$ and $C0'$, respectively), Equation (4) can be used to calculate the concentration of the analyte in the material sample S.

As one example that is not meant to limit the scope of the present disclosure, analytes are determined by absorption spectroscopy and the anticoagulation analyte is a substance that mixes with the fluid containing the analytes, and that has one or more absorption features that are detectable with an analyte detection system, such as analyte detection system 910. In some embodiments, the anticoagulation solution AC contains an anticoagulant analyte of known concentration (e.g., $C1$). In addition, the anticoagulant of this embodiment is treated as an analyte by sampling system 100, and thus has a concentration that is measured in mixture S/AC (e.g., $C1'$). The concentration of the sample analyte is measured as $C0'$, and thus the undiluted sample analyte concentration may be computed, as in Equation (4).

Some embodiments of each of the methods described herein may include a computer program accessible to and/or executable by a processing system, e.g., a one or more processors and memories that are part of an embedded system. Thus, as will be appreciated by those skilled in the art, embodiments of the disclosed inventions may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, various ones of the disclosed inventions may take the form of a method, an entirely hardware embodiment, an entirely software embodiment or an embodiment combining software and hardware aspects. Furthermore, any one or more of the disclosed methods (including but not limited to the disclosed methods of measurement analysis, interferent determination, and/or calibration constant generation) may be stored as one or more computer readable code segments or data compilations on a carrier medium. Any suitable computer readable carrier medium may be used including a magnetic storage device such as a diskette or a hard disk; a memory cartridge, module, card or chip (either alone or installed within a larger device); or an optical storage device such as a CD or DVD.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of embodiments, various features of the inventions are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Further information on analyte detection systems, sample elements, algorithms and methods for computing analyte concentrations, and other related apparatus and methods can be found in U.S. Patent Application Publication No. 2003/0090649, published May 15, 2003, titled REAGENT-LESS WHOLE BLOOD GLUCOSE METER; U.S. patent application Publication No. 2003/0178569, published Sep. 25, 2003, titled PATHLENGTH-INDEPENDENT METHODS FOR OPTICALLY DETERMINING MATERIAL COMPOSITION; U.S. Patent Application Publication No. 2004/0019431, published Jan. 29, 2004, titled METHOD OF DETERMINING AN ANALYTE CONCENTRATION IN A SAMPLE FROM AN ABSORPTION SPECTRUM; U.S. Patent Application Publication No. 2005/0036147, published Feb. 17, 2005, titled METHOD OF DETERMINING ANALYTE CONCENTRATION IN A SAMPLE USING INFRARED TRANSMISSION DATA; and U.S. Patent Application Publication No. 2005/0038357, published on Feb. 17, 2005, titled SAMPLE ELEMENT WITH BARRIER MATERIAL. The entire contents of each of the above-mentioned publications are hereby incorporated by reference herein and are made a part of this specification.

A number of applications, publications and external documents are incorporated by reference herein. Any conflict or contradiction between a statement in the bodily text of this specification and a statement in any of the incorporated documents is to be resolved in favor of the statement in the bodily text.

Although the invention(s) presented herein have been disclosed in the context of certain preferred embodiments and examples, it will be understood by those skilled in the art that the invention(s) extend beyond the specifically disclosed embodiments to other alternative embodiments and/or uses of the invention(s) and obvious modifications and equivalents thereof. Thus, it is intended that the scope of the invention(s) herein disclosed should not be limited by the particular embodiments described above.

What is claimed is:

1. A method for maintaining clear passageways in a fluid flow system connected to a patient, the method comprising:
   providing a passageway configured to carry a fluid flow in a fluid flow system from the patient;
   drawing a fluid sample into the fluid flow system;
   separating an analysis portion from the fluid sample;
   providing one or more anti-clotting agents to only the analysis portion, wherein at least one of the anti-clotting agents comprises an anticoagulant;
   preventing the analysis portion of the fluid sample from being returned to the patient; and
   analyzing the analysis portion to determine at least one analyte measurement.

2. The method of claim 1, wherein providing one or more anti-clotting agents comprises intermittently providing ultrasonic energy to the passageway.

3. The method of claim 1, wherein providing one or more anti-clotting agents comprises delivering a cleaning solution that is thermally stable at room temperatures.

4. The method of claim 1, wherein providing one or more anti-clotting agents comprises delivering a mixture having approximately 1% TERGAZYME in saline.

5. The method of claim 1, wherein providing one or more anti-clotting agents comprises delivering a mixture comprising sodium heparin.

6. The method of claim 1, wherein providing one or more anti-clotting agents comprises delivering a mixture comprising K2EDTA.

7. The method of claim 1, wherein providing one or more anti-clotting agents comprises delivering a mixture comprising K3EDTA.

8. The method of claim 1, wherein providing one or more anti-clotting agents comprises delivering a mixture comprising potassium oxalate and sodium fluoride.

9. The method of claim 1, wherein providing one or more anti-clotting agents comprises delivering a mixture comprising sodium citrate and citric acid.

10. The method of claim 1, further comprising:
    determining a ratio of volume of anticoagulant solution to total volume;
    using the equation $C0 = C0'(1 + \delta V/V0)$ to correct for dilution; and
    storing the corrected measurement in a memory.

11. The method of claim 10, further comprising:
    providing an accurately-measured volume of anticoagulant solution; and
    measuring the amount of anticoagulation analyte in the analysis portion.

12. The method of claim 1, wherein analyzing the analysis portion comprises analyzing the analysis portion for glucose concentration.

13. The method of claim 1, further comprising treating the fluid sample.

14. The method of claim 13, wherein treating comprises separating the fluid sample into fluid sample sub-components.

15. The method of claim 14, wherein separating the fluid sample into fluid sample sub-components comprises filtering the fluid sample.

16. The method of claim 14, wherein separating the fluid sample into fluid sample sub-components comprises centrifuging the fluid sample.

17. The method of claim 1, wherein providing one or more anti-clotting agents comprises introducing heparin into the analysis portion.

18. The method of claim 17, wherein introducing heparin comprises introducing a solution having a sodium heparin concentration of approximately 10 mg/dL.

19. The method of claim 1, wherein preventing the analysis portion of the analysis portion from being returned to the patient comprises directing the analysis portion into a waste reservoir.

20. A method for maintaining clear passageways in a fluid flow system connected to a patient, the method comprising:
    providing a passageway configured to carry a fluid flow in a fluid flow system from the patient;
    drawing a fluid sample into the fluid flow system;
    providing one or more anti-clotting agents to at least a portion of the fluid sample, wherein at least one of the anti-clotting agents comprises an added anticoagulant; and
    returning to the patient only one or more portions of the fluid sample, wherein the one or more portions include no added anticoagulant.

21. The method of claim 20, wherein providing one or more anti-clotting agents comprises delivering a mixture comprising sodium heparin.

22. The method of claim 20, wherein providing one or more anti-clotting agents comprises delivering a mixture comprising K2EDTA.

23. The method of claim 20, wherein providing one or more anti-clotting agents comprises delivering a mixture comprising K3EDTA.

24. The method of claim 20, wherein providing one or more anti-clotting agents comprises delivering a mixture comprising potassium oxalate and sodium fluoride.

25. The method of claim 20, wherein providing one or more anti-clotting agents comprises intermittently providing ultrasonic energy to the passageway.

26. The method of claim 20, wherein providing one or more anti-clotting agents comprises delivering a cleaning solution that is thermally stable at room temperatures.

27. The method of claim 20, wherein providing one or more anti-clotting agents comprises delivering a mixture having approximately 1% TERGAZYME in saline.

28. The method of claim 20, wherein providing one or more anti-clotting agents comprises delivering a mixture comprising sodium citrate and citric acid.

29. The method of claim 20, further comprising:
separating an analysis portion from the fluid sample; and
analyzing the analysis portion to determine at least one analyte measurement.

30. The method of claim 29, wherein analyzing the analysis portion comprises analyzing the analysis portion for glucose concentration.

31. The method of claim 29, further comprising:
determining a ratio of volume of anticoagulant solution to total volume;
using the equation $C0=C0'(1+\delta V/V0)$ to correct for dilution; and
storing the corrected measurement in a memory.

32. The method of claim 31, further comprising:
providing an accurately-measured volume of anticoagulant solution; and
measuring the amount of anticoagulation analyte in the analysis portion.

33. The method of claim 29, wherein providing one or more anti-clotting agents comprises introducing heparin into the analysis portion.

34. The method of claim 33, wherein introducing heparin comprises introducing a solution having a sodium heparin concentration of approximately 10 mg/dL.

35. The method of claim 20, further comprising treating the fluid sample.

36. The method of claim 35, wherein treating comprises separating the fluid sample into fluid sample sub-components.

37. The method of claim 36, wherein separating the fluid sample into fluid sample sub-components comprises filtering the fluid sample.

38. The method of claim 36, wherein separating the fluid sample into fluid sample sub-components comprises centrifuging the fluid sample.

39. The method of claim 20, wherein returning to the patient one or more portions of the fluid sample comprises pumping a volume of fluid sample back to the patient.

* * * * *